US005717209A

United States Patent [19]
Bigman et al.

[11] Patent Number: 5,717,209
[45] Date of Patent: Feb. 10, 1998

[54] SYSTEM FOR REMOTE TRANSMISSION OF SPECTRAL INFORMATION THROUGH COMMUNICATION OPTICAL FIBERS FOR REAL-TIME ON-LINE HYDROCARBONS PROCESS ANALYSIS BY NEAR INFRA RED SPECTROSCOPY

[75] Inventors: Joel Bigman; Irina Zilberman; Ilan Sela, all of Haifa, Israel

[73] Assignee: Petrometrix Ltd., Migdal Haemek, Israel

[21] Appl. No.: 639,659

[22] Filed: Apr. 29, 1996

[51] Int. Cl.⁶ .................................................. G01N 21/35
[52] U.S. Cl. ........................................................ 250/339.12
[58] Field of Search ....................................... 250/339.12

[56] References Cited

U.S. PATENT DOCUMENTS

| | | |
|---|---|---|
| 2,527,121 | 10/1950 | Dudenbostel, Jr. . |
| 2,527,122 | 10/1950 | Heigl et al. . |
| 3,204,105 | 8/1965 | Robinson . |
| 3,371,574 | 3/1968 | Dwyer . |
| 3,625,613 | 12/1971 | Gillespie et al. . |
| 3,782,828 | 1/1974 | Alfano et al. . |
| 3,788,742 | 1/1974 | Garbuny . |

(List continued on next page.)

FOREIGN PATENT DOCUMENTS

| | | |
|---|---|---|
| 0 285 251 | 10/1988 | European Pat. Off. . |
| 781972 | 8/1957 | United Kingdom . |

OTHER PUBLICATIONS

R. Mackison, S.J. Brinkworth, R.M. Belchamber, R.E. Aries, D.J. Cutler, C. Leeley, and H.M. Mould, "A Demonstration of Truly Remote In-line Near-Infrared Process Analysis." *Applied Spectroscopy*, vol. 46, No. 6, pp. 1020–10284, 1992.

Coate, J. et al, "The Design and Application of Spectroetric Analyzers for the Chemical Process Industry", Spectroscopy, 7(9), pp. 40–49 (Nov./Dec. 1992).

Niemezyk, T.M. et al, "Multichannel Raman Spectoscopy Tackles Industrial Problems", Laser Focus World, pp. 85–97 (Mar. 1993).

Moore, D.S. et al, "Single–Pulse Coherent Raman Spectoscopy in Shock Compressed Benzene", Proceedings of the IX Air AIRAPT Conference, Albany, NY, Jul., 1983.

Klyshko, D.N. et al, "Remote Determination of the Concentration of Impurities in Water by the Laser Spectroscopy Method with Calibration by Raman Scattering" Sov. Phys. Dokl. vol. 23 No. 1 pp. 55–57 (Jan. 1978).

Sato, T. et al, "Remote Detection of Oil Pollutants by Using a Laser Radar", Trans. IECE of Japan, vol. 61 No. 3 pp. 260–261 (Mar. 1978).

Telfair, W. et al, "A Microcomputer–Controlled Infrared Analyzer for Multi–Component Analysis", American Laboratory, vol. 8 No. 11 pp. 91–100 (Nov. 1976).

Maggard, S., "Octane", Fuel Reformulation, May/Jun. 1972 pp. 71–77.

Finch, Peter, "Near–Infrared Online Analysis of Octane Number Testing", Measurement+ Control, vol. 27, May, 1994.

*Primary Examiner*—Constantine Hannaher
*Attorney, Agent, or Firm*—Mark M. Friedman

[57] ABSTRACT

A system for remote near infra red (NIR) spectral analysis of hydrocarbons using telecommunication optical fibers for real-time on-line transmission of NIR spectral information from an examined hydrocarbon sample to a remote analyzer comprising (a) a light source for generating near infra red radiation; (b) an optical probe head being at on-line contact with an analyzed hydrocarbon sample; (c) at least one telecommunication transmitting optical fiber for inputting the near infra red radiation into the optical probe head, such that the radiation passes at least once through the hydrocarbon sample, such that a spectrum of the sample is generated; (d) a detector for analyzing the spectrum, the detector and the light source being part of an analyzer; and (e) at least one telecommunication receiving optical fiber for receiving the radiation after the passing through the sample and inputting the radiation into the detector.

29 Claims, 11 Drawing Sheets

U.S. PATENT DOCUMENTS

| | | |
|---|---|---|
| 3,850,525 | 11/1974 | Kaye . |
| 3,896,775 | 7/1975 | Chang et al. . |
| 4,045,671 | 8/1977 | Dille et al. . |
| 4,103,162 | 7/1978 | Iwamoto et al. . |
| 4,105,919 | 8/1978 | Bridges et al. . |
| 4,247,770 | 1/1981 | Welch . |
| 4,512,660 | 4/1985 | Goldberg . |
| 4,540,282 | 9/1985 | Landa et al. . |
| 4,553,032 | 11/1985 | Lo et al. . |
| 4,594,968 | 6/1986 | Degobert et al. . |
| 4,619,528 | 10/1986 | Genack et al. . |
| 4,620,284 | 10/1986 | Schnell et al. . |
| 4,674,879 | 6/1987 | Gregorig et al. . |
| 4,707,603 | 11/1987 | Miemelä et al. . |
| 4,755,054 | 7/1988 | Ferree . |
| 4,783,168 | 11/1988 | Florisson et al. . |
| 4,800,279 | 1/1989 | Hieftje et al. . |
| 4,802,761 | 2/1989 | Bowen et al. . |
| 4,856,897 | 8/1989 | Fateley et al. . |
| 4,875,771 | 10/1989 | Bowley et al. . |
| 4,886,358 | 12/1989 | Pellenbarg et al. . |
| 4,934,816 | 6/1990 | Silver et al. . |
| 4,945,249 | 7/1990 | Grant et al. . |
| 4,963,745 | 10/1990 | Maggard . |
| 4,968,887 | 11/1990 | Wong . |
| 4,980,566 | 12/1990 | Heilweil . |
| 4,986,656 | 1/1991 | Sweeney et al. . |
| 4,994,671 | 2/1991 | Safinya et al. . |
| 5,044,755 | 9/1991 | Landa et al. . |
| 5,088,820 | 2/1992 | Winefordner et al. . |
| 5,112,127 | 5/1992 | Carrabba et al. . |
| 5,121,337 | 6/1992 | Brown . |
| 5,124,553 | 6/1992 | Hilliard et al. . |
| 5,139,334 | 8/1992 | Clark . |
| 5,145,785 | 9/1992 | Maggard et al. . |
| 5,166,747 | 11/1992 | Schroeder et al. . |
| 5,175,433 | 12/1992 | Browner et al. . |
| 5,208,648 | 5/1993 | Batchelder et al. . |
| 5,218,428 | 6/1993 | Hoult . |
| 5,229,838 | 7/1993 | Ganz et al. . |
| 5,262,644 | 11/1993 | Maguire .................................. 250/339 |
| 5,303,165 | 4/1994 | Ganz et al. . |
| 5,381,237 | 1/1995 | Sela . |

FIG. 6 (Prior art)
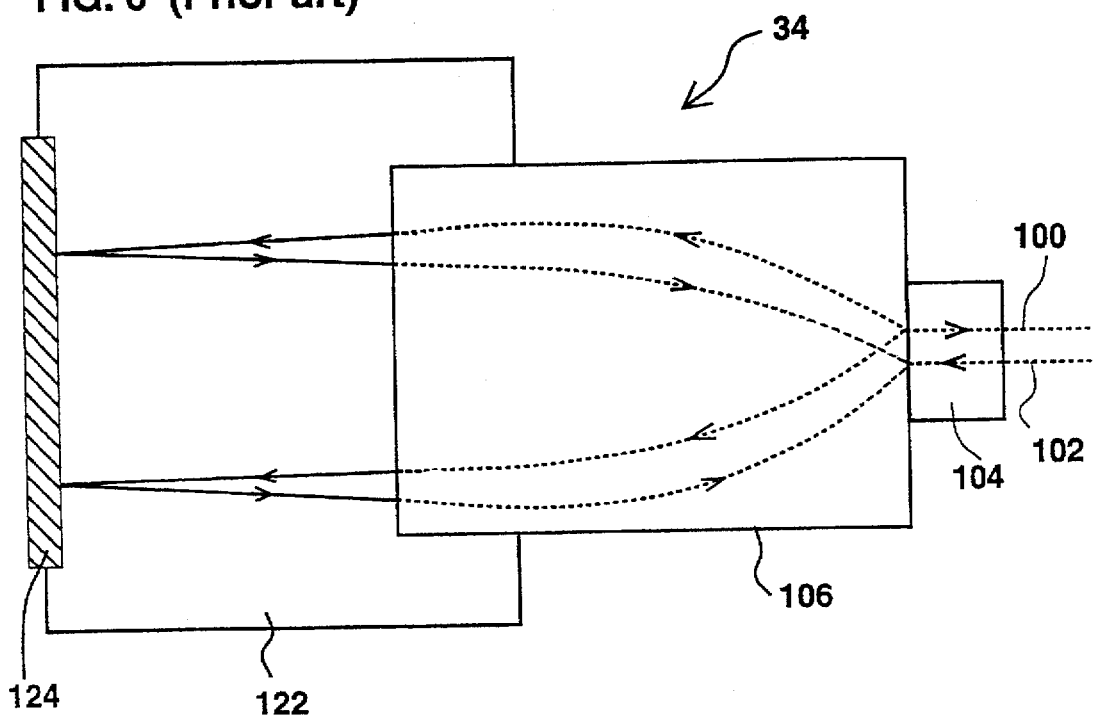
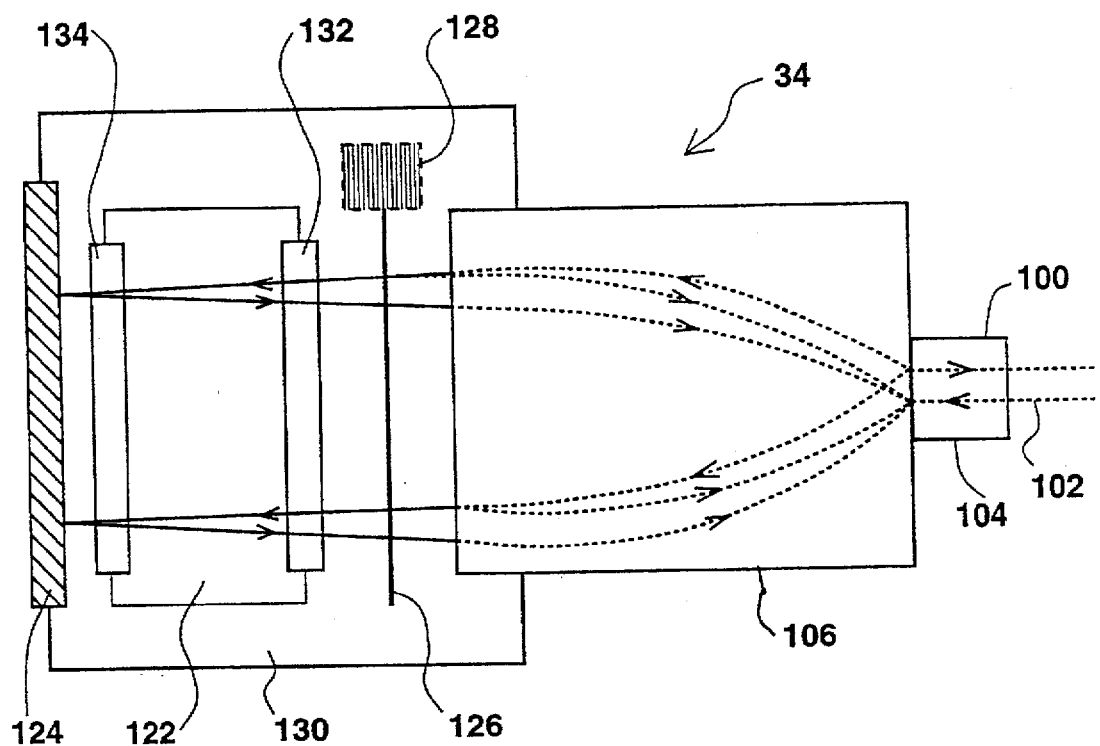
FIG. 7 (Prior art)

SYSTEM FOR REMOTE TRANSMISSION OF SPECTRAL INFORMATION THROUGH COMMUNICATION OPTICAL FIBERS FOR REAL-TIME ON-LINE HYDROCARBONS PROCESS ANALYSIS BY NEAR INFRA RED SPECTROSCOPY

FIELD AND BACKGROUND OF THE INVENTION

The present invention relates to a system for remote real-time near infra red (NIR) spectral analysis of hydrocarbons. More particularly, the present invention relates to the use of telecommunication optical fibers for real-time on-line transmission of NIR spectral information from an examined hydrocarbon sample to a remote analyzer for determining chemical, physical and performance properties of the hydrocarbons in a fuel plant such as for example a fuel refinery, a fuel pipeline company or a petrochemical plant.

The absorption of light by a sample, as a function of wavelength, forms the basis of absorption spectroscopy. The analysis can take place in a number of spectral ranges, ranging from the ultraviolet and visible range, where molecules absorb light due to electronic transitions, to the infra-red range, where light absorption corresponds to vibrational transitions. In the near infra-red (NIR) region, absorption corresponds to vibrational transitions in the bonds between hydrogen atoms and the rest of the molecule (referred to as X—H bonds).

The exact wavelength at which these X—H bonds absorb light depends on the structure of the molecule. This forms the basis of analysis, as different molecules, such as aromatics, aliphatics and olefins, have different absorption spectra.

In classic laboratory analytical spectroscopy, particular peaks are identified with particular compounds of interest. Calibration curves are prepared by measuring standard solutions of the compounds, and by measuring an unknown solution's absorption at the appropriate wavelengths, its concentration can be determined. If there are a number of compounds in the unknown solution, and their absorption spectra overlap, it may be impossible to determine concentrations, without subjecting the sample to a separation procedure. Other interferents, such as particulates and water, may also need to be removed before analysis can be performed.

NIR methods essentially measure the chemical makeup of a sample. Physical properties, such as distillation point, vapor pressure or cloud point, and performance properties, such as motor- (MON) and research- (RON) octane numbers, are themselves functions of the chemical makeup of the sample. The same instrument can thus be calibrated using suitable mathematical methods to determine a wide variety of parameters of interest to the petrochemical industry, some of which are listed in Table 1 below.

Advanced control systems such as ones employed to control processes in fuel refineries and in petrochemical plants need accurate real-time data in order to enable accurate response to changes in various processes parameters.

Near Infra Red (NIR) technology holds the promise of real-time on-line analysis of physical, chemical and performance properties of hydrocarbons. This technology overcomes the major problems associated with classic methods of analysis, such as gas chromatography, for analyzing chemical properties, or specific analyzers for analyzing physical and performance properties, such as the knock engine for octane number determination.

| Chemical Composition | Physical and Performance Properties | |
| --- | --- | --- |
| total aromatics volume % | motor octane (MON) | freeze point |
| benzene volume % | research octane (RON) | pour point |
| MTBE[1] volume % | Reid vapor pressure[3] | flash point |
| total olefins volume % | viscosity | cloud point |
| PIONA[2] | API[4] gravity[5] | distillation points |

[1]Methyl tertiary butyl ether
[2]Paraffins, Isomers, Olefins, Naphthenes, Aromatics
[3]ASTM D323
[4]American Petroleum Institute
[5]ASTM D287-67 or D1298-80.

Thus, NIR instruments are used to give real-time on-line data for hydrocarbon physical, chemical and performance properties, that until now have involved long lag times between sampling and determination of critical parameters, due to the physical limitations of the analysis techniques. Hence, NIR brings a new dimension to the process monitoring, process control, and process optimization domains in the fuel industry.

A number of devices which are available for use in the spectral analysis of remote sensing are known in the art. Various of these devices may be used to measure the reflection, the transmission, the fluorescence or the light scattering from the remote samples.

Such devices are typically made up of three parts. Such systems feature an analyzer, which include a light, or other radiation, source and a detection system. A second component is an optical probe head of an appropriate type, for transmitting the light, or other radiation, to, and receiving it from, the analyzed sample. Finally, the systems feature suitable optical fibers, for guiding the light, or other radiation, between the analyzer and the probe head.

A number of different devices are used for remote sensing. At least one device, described in T. Davidson, D. Tracy, A. Lokshin, K. DeCondre, L. McDermott, The Perkin Elmer Corp. in the Pittsburgh Conference, Atlanta (1993), is a probe head capable of measuring the absolute transmission signal of the sample. The probe described therein includes dual cells, one of which is for sample while the other is a dummy reference cell. A mechanical shutter is used to alternately block and unblock the sample and reference optical paths.

Such a probe suffers from a number of disadvantages. First, the probe is made up of many optical components, such as lenses, a beam splitter, prisms, optical windows, and the like, which make it awkward, expensive and difficult to properly align. Second, the probe is inefficient in that at least ¾ of the signal is lost in the course of double pass through the beam splitter, used to split the beam to the self-reference and sample optical paths.

A typical optical probe head available on the market is disclosed in U.S. Pat. No. 5,044,755 by I. Landa et al. The probe disclosed therein is designed to measure light transmission. In this particular design, the light emerging from a fiber bundle is collimated by a lens. The optical ray is then guided through a sample cell and is reflected back to the same lens which focuses the light into the same fiber bundle. Some of the fibers are used to guide the light into the probe while some of the fibers are used to guide the light out to the detection system (i.e., analyzer).

Another type of probe, used by UOP Guided Wave Inc. and by Galileo Electro-optics Corp., is a transmission probe in which the light emerging from the fiber, whether a single fiber or a fiber bundle, is collimated by a lens which guides the light through the sample cell. On emerging from the sample cell, the ray is collected by another lens which focuses the optical ray onto a second output fiber.

Neither of the two probe types described above carries a self-reference channel for use in correcting the fiber optical response.

U.S. Pat. No. 5,112,127 by M. M. Carrabba, disclosed the design of an optical probe head for measuring Raman scattering. The device described therein is made up of many optical elements, including three lenses, a beam splitter, a filter and a prism. The device is difficult to align and is capable of probing only very small sample volumes, which may be adequate for sampling opaque materials but is undesirable for applications involving transparent liquids.

S. D. Schwab and R. L. McCreery, in Anal. Chem. 56, 2199 (1984), disclose a simple design for a Raman probe having no optical elements. A fiber bundle is used, with the inner fiber serving in the excitation while the outer fibers are used to collect the scattered light. To use the device, the bundle tip is simply immersed into the specimen to be sampled. One disadvantage of this probe is that, because of the large acceptance angle of the fibers, the device picks up room light, which, even at very low light levels, can be much stronger than the Raman signal.

U.S. Pat. No. 5,381,237, to Sela which is incorporated by reference as fully set forth herein, discloses devices and methods for determining optical properties related to a remote specimen. The devices described therein are optical probe heads suitable for measuring transmission spectra, index of refraction, Raman and Rayleigh scattering, and fluorescence spectra and are suitable for applications in harsh environments, does not require sample preparation, can be operated in self-referencing configurations and can provide absolute signals, utilizing optical fibers for remote real time on-line measurements in hazardous environments. Some or all of these and other features of the invention by Sela are achieved in various embodiments through the utilization of a single gradient index (GRIN) lens which is rigidly connected to the polished side of an optical fiber, and, depending on the exact application in question, through the addition of certain accessories.

According to one of the embodiments of the optical probe head of Sela, the head is for determining the absorption spectrum of a sample and includes (a) a gradient index lens at least one face of which is in contact with the sample; (b) a mirror placed so as to reflect radiation coming through the gradient index lens back to the gradient index lens through the sample; (c) a transmitting optical fiber for inputting radiation into the gradient index lens; and (d) a receiving optical fiber. The transmitting and receiving optical fibers are fixedly held relative to the gradient index lens so that the gradient index lens and the optical fibers are aligned such that radiation input into the gradient index lens by the transmitting optical fiber which passes through the gradient index lens and the sample to the mirror is reflected by the mirror through the sample and through the gradient index lens and is received by the receiving optical fiber.

According to another embodiment of the optical probe head of Sela, the head is for determining the absolute transmission or absorption of a sample and further includes a moveable partition located between the gradient index lens and the mirror, the partition serving to alternately block and unblock radiation between the mirror and the gradient index lens and thereby when the moveable partition is not blocking radiation between the mirror and the gradient index lens, radiation input into the gradient index lens by the transmitting optical fiber which passes through the gradient index lens and the sample to the mirror is reflected by the mirror through the sample and through the gradient index lens and is received by the receiving optical fiber.

The probe heads disclosed by Sela can be used in conjunction with any of a wide variety of analyzers and optical fibers systems in transmission spectroscopy, Raman spectroscopy, and in index of refraction measurements.

Pure silica core optical fibers are the ones currently used for remote optical spectroscopy due to their wide transmission band. Although silica, in principle, has a wide optical transmission band, in practice there are major difficulties with this material.

A pure silica based fiber has adsorbed water molecules, that often interfere with light transmission at crucial wavelengths. Even "low OH" or low water silica fibers have some adsorbed water molecules that interfere with the measurements (see, Fiberguide industries, 1 Bay St. Stirling, N.J. 07980, Cat. "Anhydroguide G" low OH Vis-IR fiber). Furthermore, this absorption results in much higher losses through the fiber, thus limiting the length through which spectroscopy can practically be performed. In addition, the absorption peak changes with temperature, thus making interpretation of spectral data difficult.

The water adsorbed in pure silica fibers absorbs light at a wavelength that is crucial in many spectroscopic applications including those of hydrocarbons. The water peak falls at 940 nm and interferes with for example the $CH_2$ absorption peak at 936 nm, and in fact also with neighboring absorption peaks as well.

Telecommunication (doped silica) optical fibers, on the other hand, are characterized by a relatively narrow effective transmission range (e.g., 800–1,600 nm) and are therefore regarded as not suitable for transmission of wide spectral information. In fact Mackison et al., in R. Mackison, S. J. Brinkworth, R. M. Belchamber, R. E. Aries, D. J. Cutler, C. Deeley and H. M. Mould (1992) A demonstration of truly remote on-line near infrared process analysis. Applied Spectroscopy 46, 1020–1024, see page 1021 therein, teach away the use of telecommunication optical fibers for transmission of spectral information, due to their small diameter. Nevertheless, use of telecommunication fibers for remote sensing could have advantages over pure silica fibers since they are characterized by (a) no interfering absorption peaks; (b) no sensitivity to environmental factors, such as temperature; (c) ability to measure through long lengths of fiber (up to 2 miles) if the appropriate spectral range is selected and, last but not least (d) a much lower cost (e.g., 5–10 fold lower as compared with pure silica core optical fibers). A further advantage is that many fuel plants have existing optical fibers installed, so fiber installation may be completely avoided.

There is thus a widely recognized need for, and it would be highly advantageous to have, a system for NIR spectral analysis of hydrocarbons in which telecommunication optical fibers are used for remote, real-time and on-line transmission of NIR spectral information from an examined hydrocarbon sample to a detector for determining chemical, physical and performance properties of the hydrocarbons.

Many properties (i.e., physical, chemical and performance parameters) of hydrocarbon mixtures can be determined by analyzing the optical absorption of the mixtures. These properties are related to the spectral data through a calibration process. Spectral data, and the associated "property" data, that is, a property of interest, are used to create a "model" which mathematically relates the two. The model is typically a linear model, generated with a program such as Unscrambler (CAMO A/S, Olav Tryggvasonat 24, N-7011 Trodhein, Norway). Thus, all presently known optically based analyzers include a linear mathematical model for relating the spectral information to the desired parameters.

Linear mathematical models for relating the spectral information to the desired parameters (i.e., properties) include but are not limited to models disclosed in (i) Jeffrey J. Kelly and James B. Callis (1990) Nondestructive analytical procedure for simultaneous estimation of the major classes of hydrocarbon constituents of finished gasolines, Analytical Chemistry 62:1444–1451; (ii) Jeffrey J. Kelly, Clyde H. Barlow, Thomas M. Jinguji and James B. Callis (1989) Prediction of gasoline octane numbers from near infrared spectral features in the range 660–1215 nm. Anal. Chem. 61, 313–320; (iii) EP 0 285 251 A1 by BP Chemicals Ltd.; (iv) Stephen J. Swarin ad Charlene A. Drumm (1991) Prediction of gasoline properties with near infrared spectroscopy and chemometrics, SAE technical paper series 912390, the international fuels and lubricants meeting and exposition, Toronto, Canada, Oct. 7–10, 1991, 400 Commonwealth drive, Warrendale, Pa. 15096 U.S.A; (v) Peter Finch (1994) near infrared on line analysis of octane number testing. Measurement+Control 27 and John B. Cooper, Kent Wise, James Groves and William T. Welch (1995) Determination of octane numbers and Reid vapor pressure of commercial petroleum fuels using FT-Raman spectroscopy and partial least square regression analysis, all are incorporated by reference as if fully set forth herein.

Octane number is a performance property of hydrocarbon fuels that expresses the anti-knock qualities of the fuel. However, it is well known that the octane number of a hydrocarbon mixture is a non-linear function of the octane numbers of its components, see, C. T. Baird IV, Guide to Petroleum Product Blending, page. 17, HPI Consultants, Austin, Tex., 1989, and Modem Petroleum Technology, Part II, 5th edition, Edited by G. D. Hobson, John Wiley and Sons, 1984, page 787.

Therefore, linear mathematical models are of limited accuracy in determining octane numbers, as a result of this non-linear behavior.

There is thus a widely recognized need for, and it would be highly advantageous to have a non-linear mathematical model for determining the octane number of a fuel sample using NIR spectroscopy.

As mentioned above, devices which are available for use in the spectral analysis of remote sensing are typically made up of three parts: an analyzer, an optical probe head and suitable optical fibers.

Nevertheless, beside the mentioned optical fibers used for guiding the radiation between the probe head and the analyzer, at least one additional connection between the analyzer and the probe head is required for controlling the operation of the probe head. All prior an devices described hereinabove employ electrical cables to achieve the desired control and to provide the optical probe head with electrical power for its operation.

Nevertheless, laying electrical cables in the hazardous regions of a fuel plant is a complicated task since such cables should be sheltered in special complicated and expensive to build conduits, due to safety requirements as to protect against explosions.

Furthermore, at the location of the probe itself (i.e., on-line), pre-existing sheltered electrical cables are used for various other purposes, which pre-existing cables may additionally be used to provide the probe with the electrical power required for its operation.

There is thus a widely recognized need for, and it would be highly advantageous to have means other than electrical cables to connect between the analyzer and optical probe head for control reasons, which means do not involve transmission of electricity and therefore do not require a complicated installation.

SUMMARY OF THE INVENTION

According to the present invention there is provided a system for remote near infra red (NIR) spectral analysis of hydrocarbons using telecommunication optical fibers for remote, real-time and on-line transmission of NIR spectral information from an examined hydrocarbon sample to an analyzer.

According to further features in preferred embodiments of the invention described below, the system comprising (a) a light source for generating near infra red radiation; (b) an optical probe head being at on-line contact with an analyzed hydrocarbon sample; (c) at least one telecommunication (i.e., doped silica, graded index) transmitting optical fiber for inputting the near infra red radiation into the optical probe head, such that the radiation passes at least once through the hydrocarbon sample, such that a spectrum of the sample is generated; (d) a detector for analyzing the spectrum, the detector and the light source being part of an analyzer; and (e) at least one telecommunication receiving optical fiber for receiving the radiation after its passing through the sample and inputting the radiation into the detector.

According to still further features in the described preferred embodiments the light source includes (a) an illuminator for the generation of the radiation, which radiation is propagating in a parallel fashion, as effected by a suitable convex lens; (b) a motor operated filter wheel for wavelength calibration; (d) a collimating optical system for directing the radiation into the transmitting optical fiber.

According to still further features in the described preferred embodiments the system further comprising one additional optical probe head being off-line in a general purpose area of a fuel plant and being in spectral communication with the analyzer via additional telecommunication optical fibers, the one additional optical probe head being for manual analysis of the hydrocarbons.

According to still further features in the described preferred embodiments the collimating optical system includes a first gradient index lens.

According to still further features in the described preferred embodiments the at least one transmitting optical fiber is held in a first ferule which is connected to the first gradient index lens.

According to still further features in the described preferred embodiments the optical probe head includes (a) a second gradient index lens at least one face of which is in optical contact (i.e., direct or indirect contact) with the hydrocarbon sample; (b) a mirror placed so as to reflect radiation coming through the second gradient index lens back to the second gradient index lens through the hydrocarbon sample, wherein, the at least one transmitting optical fiber is for inputting radiation into the second gradient index lens of the optical probe head, and the at least one transmitting optical fiber and the at least one receiving optical fiber are fixedly held relative to the second gradient index lens, so that the second gradient index lens and the optical fibers are aligned, such that radiation input into the second gradient index lens by the transmitting optical fiber which passes through the second gradient index lens and the hydrocarbon sample to the mirror is reflected by the mirror through the hydrocarbon sample and through the second gradient index lens, and is received by the at least one receiving optical fiber.

According to still further features in the described preferred embodiments the optical probe head includes (c) a moveable partition located between the second gradient index lens and the mirror, the partition serving to alternately block and unblock radiation between the mirror and the second gradient index lens, wherein, the at least one transmitting optical fiber is for inputting radiation into the second gradient index lens, and the at least one transmitting optical fiber and the at least one receiving optical fiber are fixedly held relative to the second gradient index lens so that the second gradient index lens and the optical fibers are aligned such that radiation input into the second gradient index lens by the transmitting optical fiber which passes through the second gradient index lens and the hydrocarbon sample to the mirror is reflected by the mirror through the hydrocarbon sample and through the second gradient index lens and is received by the at least one receiving optical fiber when the moveable partition is not blocking radiation between the mirror and the second gradient index lens and such that radiation input into the gradient index lens by the transmitting optical fiber which is reflected from the interface of the gradient index lens and the sample is received by the at least one receiving optical fiber.

According to still further features in the described preferred embodiments the at least one transmitting optical fiber and the at least one receiving optical fiber are held in a second ferule which is connected to the second gradient index lens.

According to still further features in the described preferred embodiments the aligning of the optical fibers and the second gradient index lens is effected by introducing radiation through one of the optical fibers, moving the optical fibers and the second gradient index lens relative to each other until maximum radiation intensity is detected in the other of the optical fibers and fixing the position of the optical fibers and the second gradient index lens.

According to still further features in the described preferred embodiments the optical probe head includes a sample cell for accommodating the analyzed hydrocarbon sample, the cell includes a first and a second transparent windows, the at least one face of the second gradient index lens is in indirect contact with the hydrocarbon sample through the first window and the mirror is behind the second window.

According to still further features in the described preferred embodiments each of the first and second windows includes a material having a low surface free energy.

According to still further features in the described preferred embodiments the material having a low surface free energy is transparent TEFLON (which is a trademark of a fluorocarbon polymer.

According to still further features in the described preferred embodiments the sample cell includes a top and a bottom, a hydrocarbon inlet, a top hydrocarbon outlet located at the top and a bottom hydrocarbon outlet located at the bottom, the bottom hydrocarbon outlet is narrower than the top hydrocarbon outlet and serves for removal of pollutants accumulating at the bottom, such that pollutants are at least partially removed from the top of the cell and such that the passing of the radiation through the hydrocarbon sample is in a pollutants reduced zone.

According to still further features in the described preferred embodiments the system comprising (a) a light source for generating light radiation; (b) an optical probe head being at on-line contact with an analyzed hydrocarbon sample, wherein the optical probe head includes a sample cell for accommodating the analyzed hydrocarbon sample, the cell includes a top and a bottom, a hydrocarbon inlet, a top hydrocarbon outlet located at the top and a bottom hydrocarbon outlet located at the bottom, the bottom hydrocarbon outlet is narrower than the top hydrocarbon outlet and serves for removal of pollutants accumulating at the bottom, such that pollutants are at least partially removed from the top of the cell and such that the passing of the radiation through the hydrocarbon sample is through a pollutants reduced zone; (c) at least one transmitting optical fiber for inputting the light radiation into the optical probe head, such that the radiation passes at least once through the hydrocarbon sample and a spectrum of the hydrocarbon sample is generated; (d) a detector for analyzing the spectrum, the detector and the light source being part of an analyzer; and (e) at least one receiving optical fiber for receiving the radiation after the passing of the radiation through the sample and inputting the radiation into the detector.

According to still further features in the described preferred embodiments the system comprising (a) a light source for generating light radiation; (b) an optical probe head being at on-line contact with an analyzed hydrocarbon sample; (c) at least one transmitting optical fiber for inputting the light radiation into the optical probe head, such that the radiation passes at least once through the hydrocarbon sample, such that at least some of the radiation is absorbed by the hydrocarbon sample and a spectrum associated with the sample is generated; (d) a detector for analyzing the spectrum, the detector and the light source being part of an analyzer; (e) at least one receiving optical fiber for receiving the radiation after the passing through the sample and inputting the radiation into the detector; and (f) at least one controlling optical fiber connecting between the analyzer and the optical probe head for controlling the optical probe head.

According to still further features in the described preferred embodiments provided is a method of determining the octane number of a hydrocarbon sample comprising the steps of (a) using an optical system having a sample cell for accommodating the hydrocarbon sample, the optical system is for collecting absorption spectral data of the hydrocarbon sample; and (b) using the spectral data for calculating the octane number of the hydrocarbon by a non-linear model.

According to still further features in the described preferred embodiments the non-linear model is obtained by training an artificial neural network.

According to still further features in the described preferred embodiments the training of the artificial neural network is effected by (a) providing the artificial neural network with a training set of data, the training set of data are principal components establishing a regression relationship between spectral data and hydrocarbon octane properties of various hydrocarbon samples, the principal components contain the most relevant information, such that the components represent the main systematic variation among the various hydrocarbon samples of the training set of data, the principal components are calculated using a linear-algorithm; and (b) providing the artificial neural network with a test set (i.e., validation set) of data, such that the artificial neural network processes the training set of data for optimizing the accuracy in predicting octane properties of the test set of data.

According to still further features in the described preferred embodiments the use of the linear algorithm includes collecting reference spectral data, the reference spectral data being the absorption spectrum of the optical system, without the sample cell, the linear algorithm is further used by (i) preprocessing each of the samples spectral data by subtracting the reference spectral data for obtaining preprocessed samples spectral data; (ii) determining baselines for each of the preprocessed samples spectral data by removing high frequency components from the preprocessed samples spectral data, and leaving low frequency components of the preprocessed samples spectral data; (iii) performing baseline corrections by subtracting the baselines from the preprocessed samples spectral data for obtaining base line corrected samples spectral data; (iv) smoothing the base line corrected samples spectral data by removing high frequency noise for obtaining a smoothed samples spectral data; (v) integrating the smoothed samples spectral data; (vi) normalizing the smoothed samples spectral data by dividing each point in the smoothed samples spectral data by the integrals for obtaining normalized samples spectral data; and (vii) relating the normalized samples spectral data with hydrocarbon octane properties of the various hydrocarbon samples and deriving the principal components containing the most relevant information.

According to still further features in the described preferred embodiments the linear algorithm is selected from the group consisting of a principle component regression algorithm and a partial least square algorithm.

It is one object of the invention to provide a remote sensing system for determining properties of a hydrocarbon sample.

It is another object of the invention to provide a system for NIR spectral analysis of hydrocarbon in which telecommunication optical fibers are used for real-time on-line transmission of NIR spectral information from an examined hydrocarbon sample to an analyzing detector for determining chemical, physical and performance properties of the hydrocarbon hydrocarbons.

It is yet another object of the invention to provide a non-linear mathematical model for determining the octane number of a hydrocarbon sample.

It is yet another object of the invention to provide means other than electrical cables to connect between the analyzer and optical probe head for control reasons, which means do not involve transmission of electricity and therefore do not require a complicated installation.

It is yet another object of the invention to provide a sample cell which is less influenced by impurities such as particulates, water and inhomogeneities in the examined sample.

The present invention successfully addresses the shortcomings of the presently known configurations (i) by providing a remote sensing system for determining properties of a hydrocarbon sample, using NIR spectral analysis of the hydrocarbon sample in which telecommunication optical fibers are used for real-time on-line transmission of NIR spectral information from the examined hydrocarbon sample to an analyzing detector, (ii) by providing controlling optical fibers used for communicating between the analyzer and the optical probe head, (iii) by providing an improved sample cell less influenced by impurities, and (iii) by providing a non-linear mathematical model for determining the octane number of a hydrocarbon sample.

BRIEF DESCRIPTION OF THE DRAWINGS

The invention herein described, by way of example only, with reference to the accompanying drawings, wherein:

FIG. 6 is a schematic depiction of the optical probe head according to U.S. Pat. No. 5,381,237, used as a single beam transmission optical probe head;

FIG. 7 is a schematic depiction of the optical probe head according to U.S. Pat. No. 5,381,237, used as a dual beam transmission optical probe head;

DESCRIPTION OF THE PREFERRED EMBODIMENTS

Figure 1:
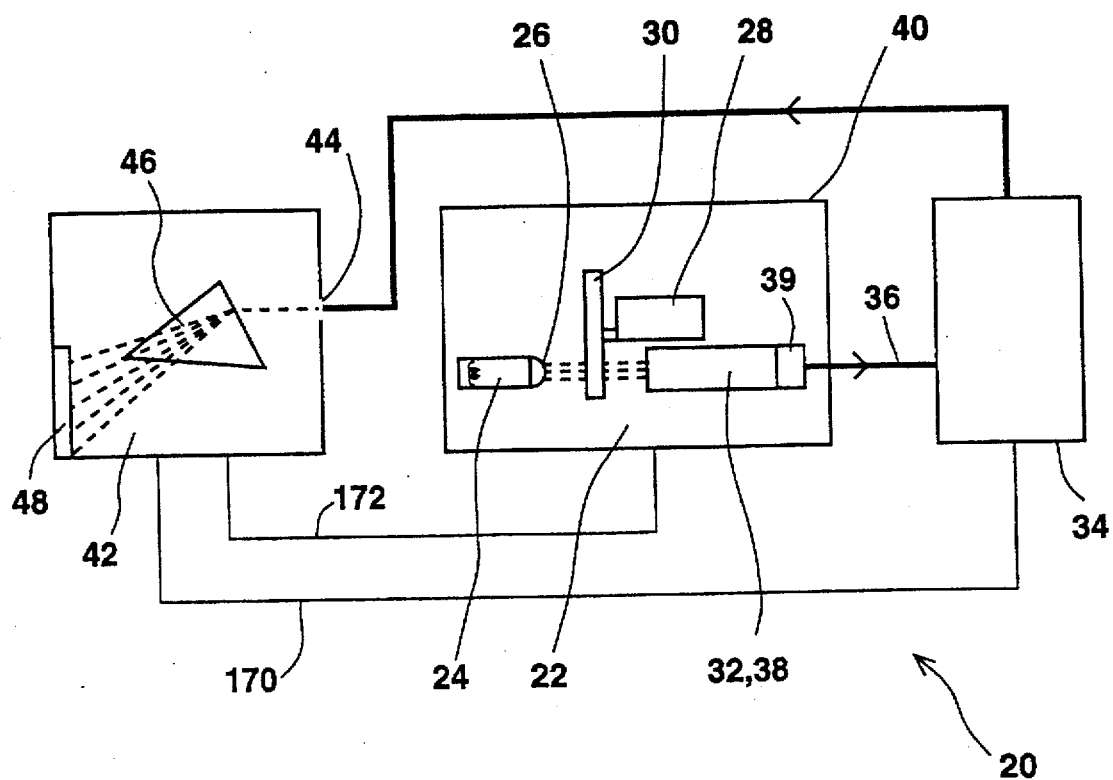
FIG. 1 is a schematic presentation of the basic construction of the remote sensing system of the present invention.

The present invention is of a system for remote near infra red (NIR) spectral analysis of hydrocarbons such as fuel using telecommunication optical fibers for real-time, on-line transmission of NIR spectral information from an examined hydrocarbon sample to a remote analyzer. The system can be used for determining chemical, physical and performance properties of the analyzed hydrocarbons. Specifically, the present invention can be used to determine the motor octane number (MON), research octane number (RON), Reid vapor pressure (ASTM D323), viscosity, API gravity (ASTM D287-67 or D1298-80), freeze point, pour point, flash point, cloud point, distillation point, fraction of total aromatics volume, fraction of benzene volume, fraction of MTBE (Methyl tertiary butyl ether) volume, fraction of olefins volume, PIONA (Paraffins, Isomers, Olefins, Naphthenes, Aromatics), and the like parameters of hydrocarbons such as fuels in for example fuel refineries and fuel pipelines.

NIR spectroscopy (i.e., 800–1,800 nm) and mid infra red (MIR, >1,800 nm) as well as the visible and ultra violet ranges (<800 nm) may all be used for determining chemical, physical and performance parameters of various materials including hydrocarbons. Nevertheless, as disclosed by Kelly et al., Jeffrey J. Kelly and James B. Callis (1990) Nondestructive analytical procedure for simultaneous estimation of the major classes of hydrocarbon constituents of finished gasolines, Analytical Chemistry 62:1444–1451, using NIR performs most accurately in determining hydrocarbons properties.

One of the reasons for the accuracy characterizing NIR in this respect is that for working at a preferred range of 0.5 AU (absorption units), a sample cell having an optical length of ca. 0.5 mm is required for MIR, whereas the optical length required when NIR spectroscopy is employed is 10–20 fold longer, since hydrocarbons absorb better MIR radiation as compared with NIR radiation.

NIR spectroscopy may be applied in a number of ways to the analysis of hydrocarbon liquid process streams in the chemical and fuel industry.

The first option is the traditional "off-line" analysis. A sample is drawn from the process stream and manually taken to the laboratory for analysis. This approach has a serious drawback since the overall time taken for the analysis, including sampling, transfer of sample, analysis, and reporting of results, is long during which process conditions can change significantly.

The second option is "at-line", or "on-line" analysis. This is the most common situation today. An analyzer is situated adjacent to the process line and connected to it by a short sample line or, alternatively, the analyzer may be interfaced to the sample line/stream by a short length of optical fiber cable (10–50 m). The main disadvantages of this approach are safety and expense. The instrument must be capable of working in harsh and hazardous environments, including explosive atmospheres. This demand requires either a rugged instrument, often contained in a special nitrogen-purged box, or housing the instrument in a special analyzer shelter, with its associated costs. Because the analyzer needs to be located close to the measurement point, usually only one process stream can be monitored in real time by a single analyzer.

The third option is termed "remote on-line". The measurement is made in the process stream. Optical probes, inserted directly into the stream, are connected to a remote spectrometer by a pair of fibers. This configuration enables safety, cost and some performance advantages to be achieved. The analyzer is located in a general purpose area, remote from the process, thus eliminating the need to purge lo and air-condition the analyzer shelter. Because there is no need to have specially "ruggedized" equipment, a high-quality research grade spectrophotometer may be used. Optical multiplexing enables further cost reductions to be achieved since a single instrument can sequentially monitor several process streams.

No doubt this is the most desired system configuration, however the implementation of this configuration is not simple. Sample conditioning is impossible, probe maintenance is difficult, and there is a limitation on the signal-to-noise ratio which can be achieved using this configuration. The type and radius of fiber optic being used also affect the signal-to-noise ratio.

The fourth option, which is implemented in the system of the present invention, combines the best features from the other options. The probe itself is located close to the process stream, and runs off a sample loop. The difficulties of working in the process stream itself are avoided, sample conditioning may be added if necessary, and lag time is minimal. Most of the electronics and optics, however, are located in the main analyzer unit, which can be located up to two miles (3 kilometers) away from the probe, in a "general purpose area", such as a control room. Thus, the trouble and expense of installing the analyzer in a hazardous area are completely avoided.

The principles and operation of a system according to the present invention may be better understood with reference to the drawings and accompanying descriptions.

Referring now to the drawings, FIG. 1 schematically illustrates the basic construction of the remote sensing system of the present invention, referred to hereinbelow as system 20. System 20 includes a light source 22 for generating near infra red (NIR) radiation. In a preferred embodiment, light source 22 includes an illuminator 24 which is generating a parallel propagating radiation. A suitable illuminator 24 is a small tungsten halogen lamp such as ones manufactured by Gilway, 800 west Cummings Park, Woburn, Mass. 01801-6355, specifically model 186-1. Illuminator 24 typically includes a convex lens 26 for effecting the parallel propagation of the radiation.

System 20 further includes an optical probe head 34 which is in optical contact with an analyzed hydrocarbon sample. Preferred optical probe heads are disclosed in U.S. Pat. No. 5,381,237, to Sela which is incorporated by reference as fully set forth herein. Further descriptions of preferred optical probe heads are given hereinbelow.

System 20 further includes at least one telecommunication (i.e., doped silica, graded index) transmitting optical fiber 36 for inputting the NIR radiation into optical probe head 34, such that the radiation passes at least once through the hydrocarbon sample, such that a spectrum of the sample is generated. In a preferred embodiment, light source 22 further includes a collimating optical system 32 for directing the radiation into transmitting optical fiber 36. Collimating optical system 32 preferably includes a first gradient index (GRIN) lens 38. In a preferred embodiment, transmitting optical fiber 36 is held in a first ferule 39 which is connected to first GRIN lens 38.

System 20 further includes at least one telecommunication receiving optical fiber 40 for receiving the radiation after passing at least once through the sample and inputting the radiation into a detector 42 for analyzing the spectrum of the sample. Detector 42 is preferably a slit 44 type spectrophotometer and includes a monochromater 46 (e.g., a grating, prism, etc.) and a detector head 48, all as well known in the art. Using a slit 44 type spectrophotometer enables to collect most of the light radiation from receiving telecommunication optical fiber 40 which is typically characterized by a small diameter (e.g., 50–100 µm) and thus increases the spectral resolution and the sensitivity of system 20. This, as will be explained in greater detail below, is required due to the use of standard telecommunication optical fibers 36 and 40 for transmission of spectral information. A suitable monochromater 46 is the Monospec 18 Spectrograph manufactured by Scientific Measurement Systems. Inc., 606 Foresight Circle East, Grand Junction Colo., 81501. A suitable detector head 48 is manufactured by Hamamatsu, 1122 Ichino-cho, Hamamatsu City, Japan, Cat. No. S3903-1024Q. In a preferred embodiment, light source 22 includes a motor 28 operated filter wheel 30 for wavelength calibration of detector 42, as well known in the art of spectrometrics.

As telecommunication optical fibers 36 and 40 are of a gradient index (GRIN) type, fibers 36 and 40 are highly suited for spectral coupling with collimating optical system 32, which, as described above, preferably includes a first GRIN lens 38 and are highly suited for spectral coupling with optical probe head 34 which, as described hereinbelow, also preferably includes a second GRIN lens.

System 20 includes computing means (not shown) for controlling the operation of detector 42, light source 22 and optical probe head 34. The computing means, detector 42, and light source 22, collectively form an analyzer, are preferably implemented at a general purpose area, e.g., a control room, of the fuel plant, in a protected environment and spectrally communicate with optical probe head 34, itself located at the fuel line (i.e., on-line) in the plant, via optical fibers 36 and 40.

According to this construction of system 20, an optical multiplexing device (not shown) allows the use of tens (e.g., 25 or more) of probes with one main analyzer unit. The main analyzer unit is preferably located in the control room, and is spectrally communicating with the probes or field units throughout the refinery. The field units can monitor hydrocarbon process input or output streams, and provide data monitoring for feed-forward and for feed-back control. Each field unit can measure several different properties simultaneously in an individual stream.

One of the inventive steps according to the present invention is the use of standard telecommunication optic fibers for transmission of spectral data. It should be noted that such a use of telecommunication optic fibers is taught away by many of the art scholars, see for example R. Mackison, S. J. Brinkworth, R. M. Belchamber, R. E. Aries, D. J. Cutler, C. Deeley and H. M. Mould (1992) A demonstration of truly remote on-line near infrared process analysis. Applied Spectroscopy 46, 1020–1024.

Optical fibers so far used for remote spectroscopy were limited to pure silica core fibers due to their wide optical transmission band. However, in practice there are major difficulties with this material, whereas doped silica optical fibers, as used for telecommunication, have several advantages over these pure silica core fibers. As described in the background section, pure silica optical fibers adsorb water molecules, that often interfere with light transmission at crucial wavelengths.

Figure 2:
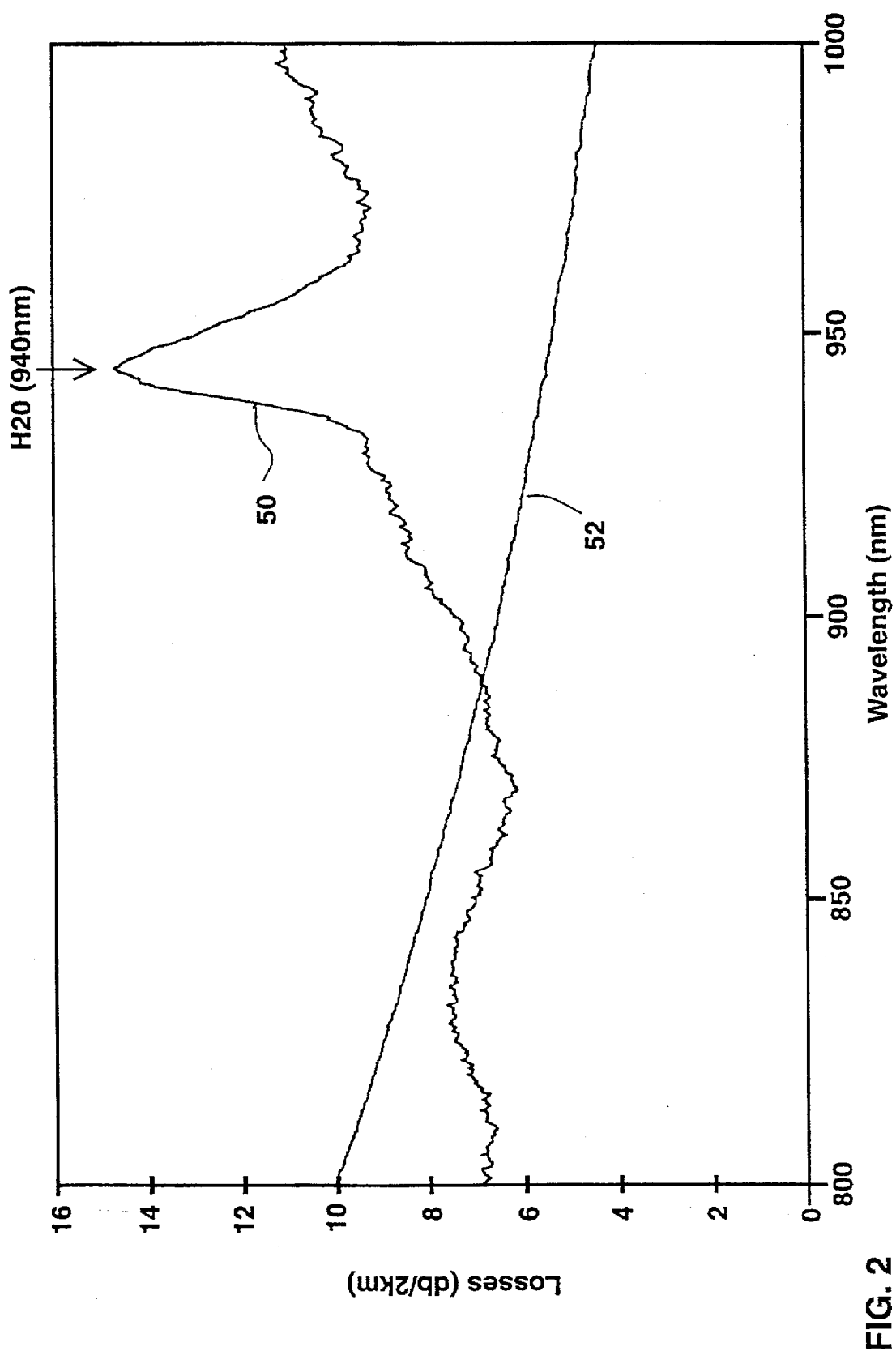
FIG. 2 presents plots of fiberoptic losses for pure silica core and telecommunication optical fibers, as measured in db/2 km, as a function of wavelengths in the NIR range.
Figure 3:
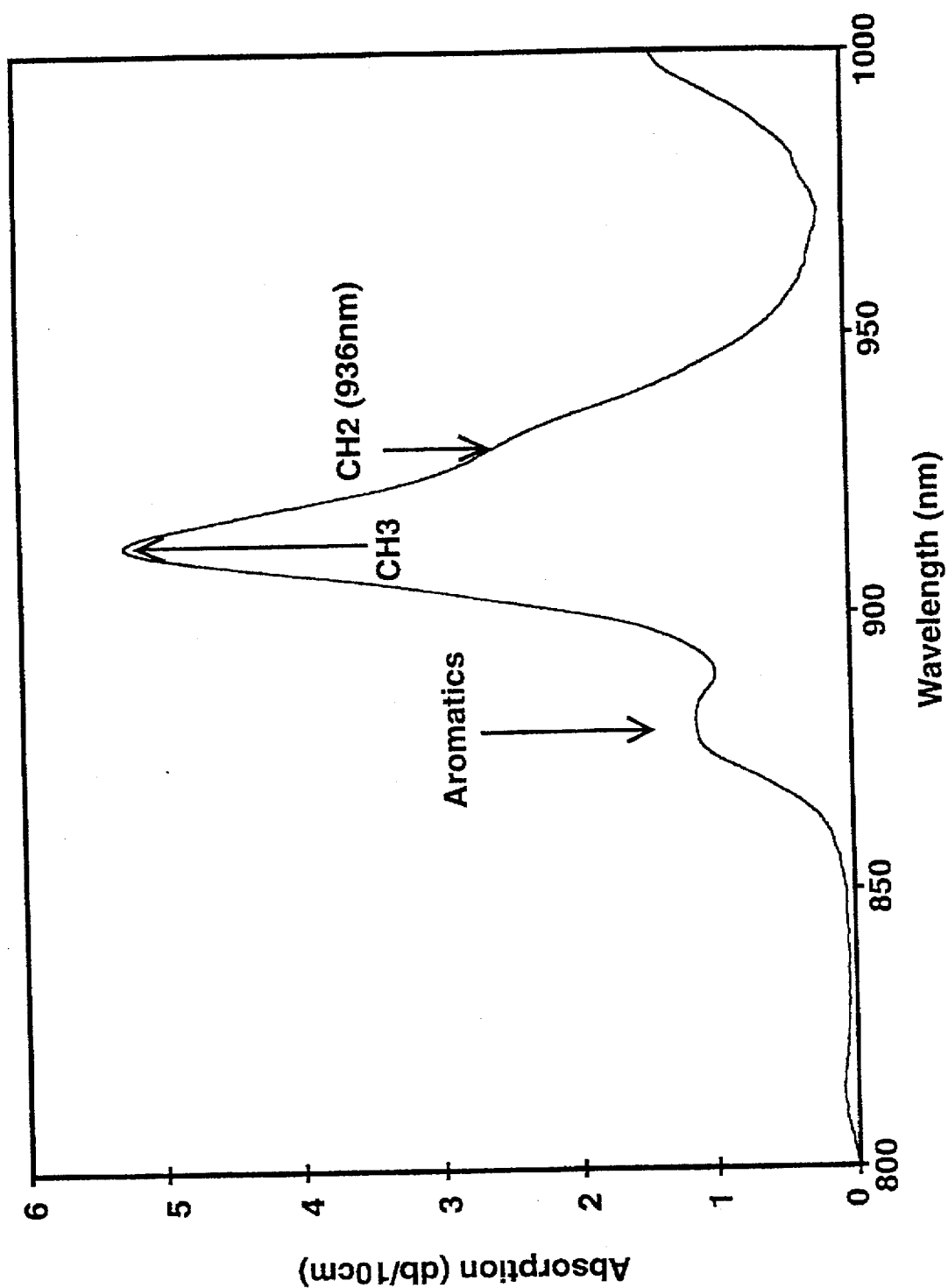
FIG. 3 is a plot depicting the absorption spectrum of hydrocarbons at the NIR range.

With reference now to FIGS. 2–3. FIG. 2 presents fiberoptic losses for silica (plot 50) and telecommunication (plot 52) optical fibers as measured in db/2 km, as a function of wavelengths in the NIR range (e.g., 800–1000 nm). The peak at 940 nm in plot 50 is due to absorption of light by water molecules in the silica fiber. This absorption results in much higher losses through the fiber, thus limiting the length through which spectroscopy can practically be performed. Comparing plot 50 and 52 at the 850–950 nm wavelength range in which most spectral information of NIR spectroscopy of hydrocarbons exists (see FIG. 3), reveals that, on the average, silica fiber losses (Ca. 11 db/2 km) are as much as three times as compared with telecommunication fiber losses (Ca. 6 db/2 km). In addition, the absorption peak at 940 nm changes with temperature (not shown), thus making interpretation of spectral data difficult.

Furthermore, as shown in FIG. 3, the water absorption characterizing pure silica fibers is at a wavelength that is crucial in many spectroscopic applications. For example, FIG. 3 shows the absorption spectrum of hydrocarbons at the NIR range. The water peak at 940 nm interferes with the $CH_2$ absorption at 936 nm, and in fact also interferes with neighboring absorptions as well, e.g., $CH_3$ and aromatics.

Despite the relatively narrow transmission range characterizing telecommunication (doped silica, graded index) fibers (i.e., 800–1,600 nm), and their small diameter (typically 50–100 μm) limiting the intensity of radiation that can be transmitted through and thus decreasing the sensitivity (i.e., signal to noise ratio), sufficient NIR spectral information is available for chemical analysis, provided that a sensitive high-quality research grade spectrophotometer is used for detection. For instance, analysis of hydrocarbon mixtures for the properties listed in Table 1 above can be performed with spectral data in this range, obtained through telecommunication optical fibers using the system f the present invention.

Telecommunication optical fibers which are graded index fibers are more suitable for this application as compared with step index fibers (e.g., pure silica fibers) as they couple light better with GRIN lenses than step index fibers. For example, graded index fibers, 100 μm core, 140 μm cladding fiber, Cat. No. ACU-MC100C, manufactured by Spectran inc., 150 Fisher drive, Avon Conn., or a similar fiber, Cat. No. 100/140 CPC3 manufactured by Corning inc., Telecommunication Products division, Corning, N.Y. 14831, are highly suitable.

Nevertheless, telecommunication graded index fibers have a smaller diameter and therefore have a relatively high associated modal noise, since the number of modes produced in a fiber is proportional to the squared radius of the fiber core, the lower this number is the greater the associated modal noise is, see, Fiber optics handbook—An introduction and reference guide to fiber optics technology and measurement techniques, 2nd edition, C. Hentschel Ed. Hewlett-Packard Gmbh, Boeblingen instruments division, Germany, 1988. Therefore, a background subtraction procedure is preferably exercised by optical probe head 34 as is described in greater detail below.

Combining NIR spectroscopy and standard telecommunication optical fibers for remote sensing of hydrocarbons is feasible since all required spectral information of hydrocarbons falls within the NIR range which is efficiently transmitted through telecommunication optical fibers, themselves devoid of the limitations characterizing pure silica fibers such as interfering absorption peaks, sensitivity to environmental factors, such as temperature, and inability to measure through long lengths of fiber, all as described above.

Using telecommunication optical fibers for remote sensing has additional advantages as follows. First the price of standard telecommunication optical fibers is Ca. ten fold lower as compared with pure silica fibers. Second, telecommunication optical fibers are easier to implement since their bending radius is smaller. Third, many off the off shelf accessories such as connectors, multiplexors, junction boxes and optical fibers splicing devices (see products Cat. of AMP incorporated fiberoptic products, Harrisburg Pa. 17105) are available for comparatively low prices for telecommunication optical fibers as compared with pure silica fibers, further lowering the cost of the system according to the present invention.

Optical probe head 34 may come in many forms. Examples include probe heads such as but not limited (i) the head disclosed in U.S. Pat. No. 5,218,428 to Hoult; (ii) the head disclosed in John Coats, Timothy Davidson and Lawrence McDermott (1992) The design and application of spectrometrics analyzers of the chemical process industry, Spectroscopy 7(9) Pages 41–49; (iii) the shuffle probe head (part No. 1SHX SO-17X) manufactured by Guided Wave Inc., 5190 Golden Foothill Parkway, El Dorado Hills, Calif. 95630; (iv) the probe disclosed in U.S. Pat. No. 4,994,671 to Safinya et al.; (v) the head disclosed in R. G. Driver, G. L. Dewey, D. A., Greenberg and J. D. Stark (1994) The sample interphase in on-line process monitoring, spectroscopy 9, 36–41; and (vi) the head disclosed in R. Mackison, S. J. Brinkworth, R. M. Belchamber, R. E. Aries, D. J. Cutler, C. Deeley and H. M. Mould (1992) A demonstration of truly remote on-line near infrared process analysis. Applied Spectroscopy 46, 1020–1024; all are incorporated by reference as if fully set forth herein.

In a preferred embodiment optical head 34 is selected from the embodiments disclosed in U.S. Pat. No. 5,381,237, to Sela, incorporated by reference.

Figure 4:
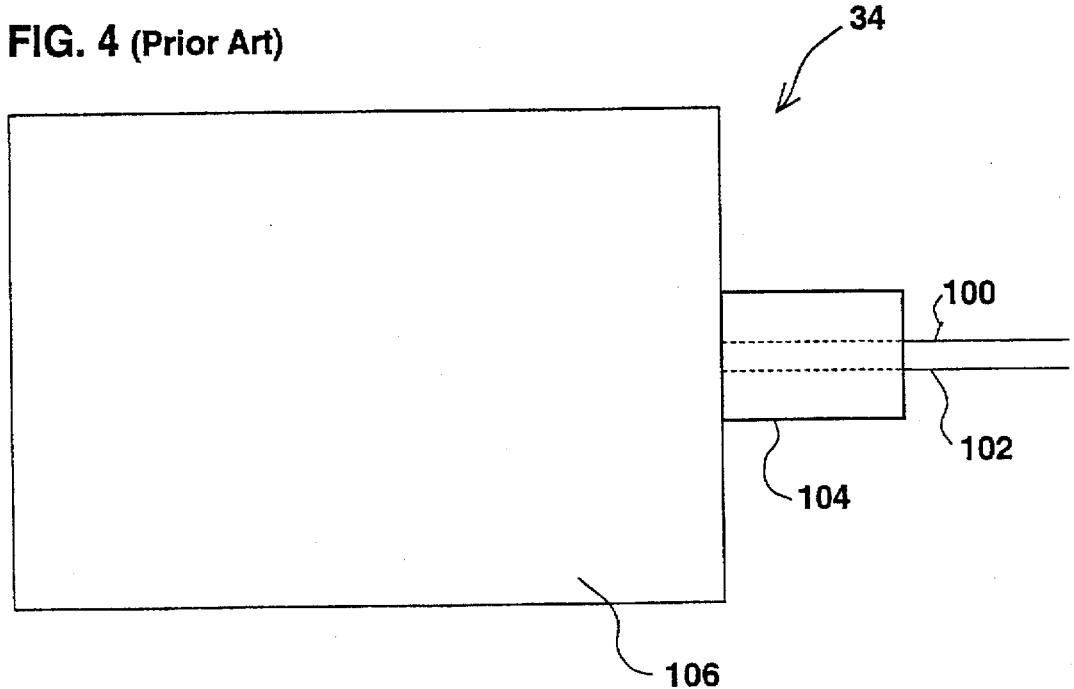
FIG. 4 is a schematic depiction showing the main components of an optical probe head according to U.S. Pat. No. 5,381,237.

FIG. 4 illustrates the basic components of an optical probe head according to U.S. Pat. No. 5,381,237. A pair of optical fibers 100 and 102 are inserted in a second ferule 104 which is rigidly connected, as by gluing, following alignment as described below, with a second gradient index (GRIN) lens 106. The pitch of GRIN lens 106 is chosen so that the light emerging from optical fiber 100 is collimated.

Figure 5:
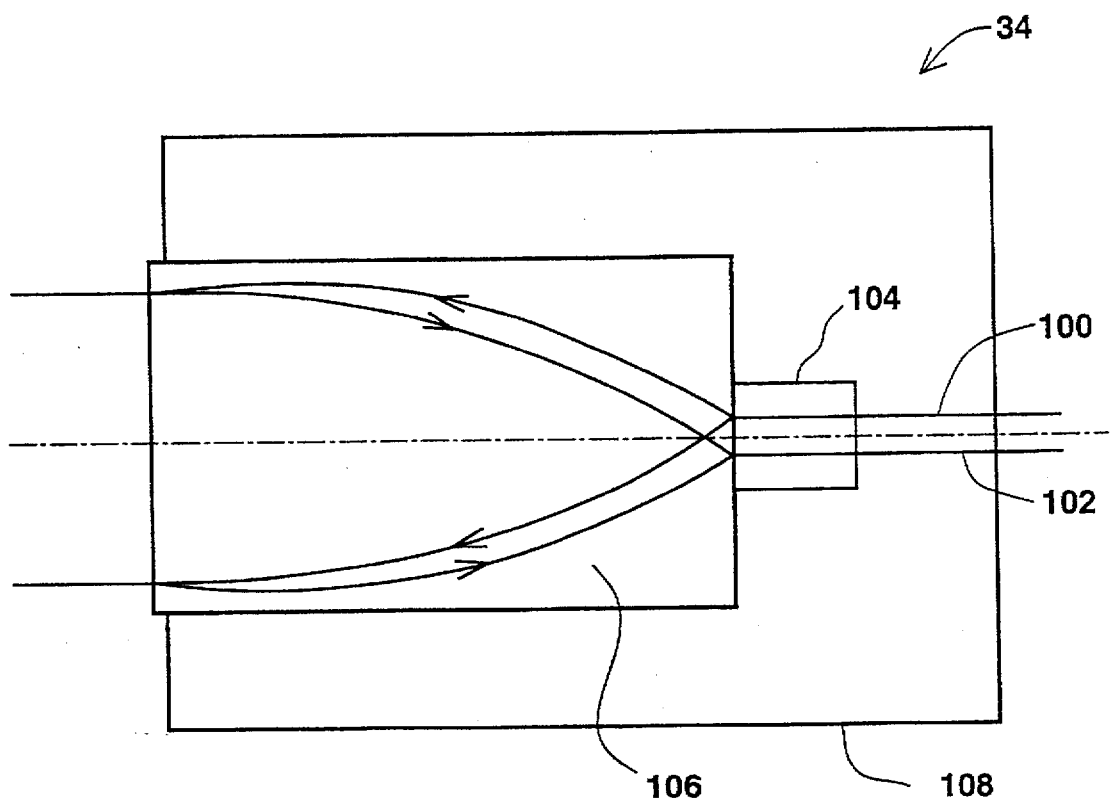
FIG. 5 is a schematic depiction of the optical probe head according to U.S. Pat. No. 5,381,237, used as an index of refraction optical probe head.

Shown in FIG. 5 is one illustration of a probe as it might appear when serving as a single beam index of refraction optical probe head. As can be seen, the probe of FIG. 5 includes the probe depicted in FIG. 4 which is partly enclosed in a housing 108. Light from the light source (not shown) is guided through fiber 100 and emerges from fiber 100 into second GRIN lens 106. GRIN lens 106 collimates the light emerging from fiber 100. A portion of the light is reflected back from the interface between the sample and GRIN lens 106. The specular reflected signal is focused back into optical fiber 102 which guides the optical signal to the detector (not shown).

As is readily apparent from the description above, it is crucial to properly align the device to ensure that reflected signal is properly focused into optical fiber 102, the alignment can be effected in a number of ways as further described in U.S. Pat. No. 5,381,237.

Shown in FIG. 6 is a probe head according to U.S. Pat. No. 5,381,237 for measuring the absorption spectrum of samples. Light from the light source is guided through optical fiber 100. The light is collimated by second GRIN lens 106 and passes through a sample cell 122. At the far end, the light is reflected by a mirror 124 and proceeds to pass through sample cell 122 and second GRIN lens 106 in the reverse sense. Second GRIN lens 106 focuses the reflected light into optical fiber 102 which guides the light to the signal analyzer system (not shown).

Shown in FIG. 7 is a probe head according to U.S. Pat. No. 5,381,237 for measuring transmission but which is self-referencing (i.e., performs background subtraction). The probe head is aligned so that the reflection from mirror 124 is focused into optical fiber 102. A suitable partition 126, preferably located in front of the sample cell 122 within a housing 130, and operated by some suitable means such as a solenoid 128, is used to alternately block and unblock the optical axis or path of the light. Sample cell 122 features optical windows 132 and 134 on its front and back surfaces. Approximately 5% of the signal is reflected back from the near surface of GRIN lens 106 into optical fiber 102. This portion of the signal is not transferred through the sample and is used for self-referencing the device.

Sample cells usually used in spectroscopy consist of a long, narrow tube, with windows at either end. This design is not suitable for on-line process measurements, for a number of reasons as follows. First, bubbles can collect in the cell, interfering with the optical path. Second, water and dirt can settle in the bottom of the cell, eventually building up and interfering with the optical path. Third, the cell's windows tend to collect dirt or "muck" that interferes with the measurement.

Due to the poor absorption of most hydrocarbons in the spectral range that is accessible through telecommunication optical fibers, a sample cell with a long optical path length is possible. This can result in several advantages, as described hereinbelow.

Figure 8:
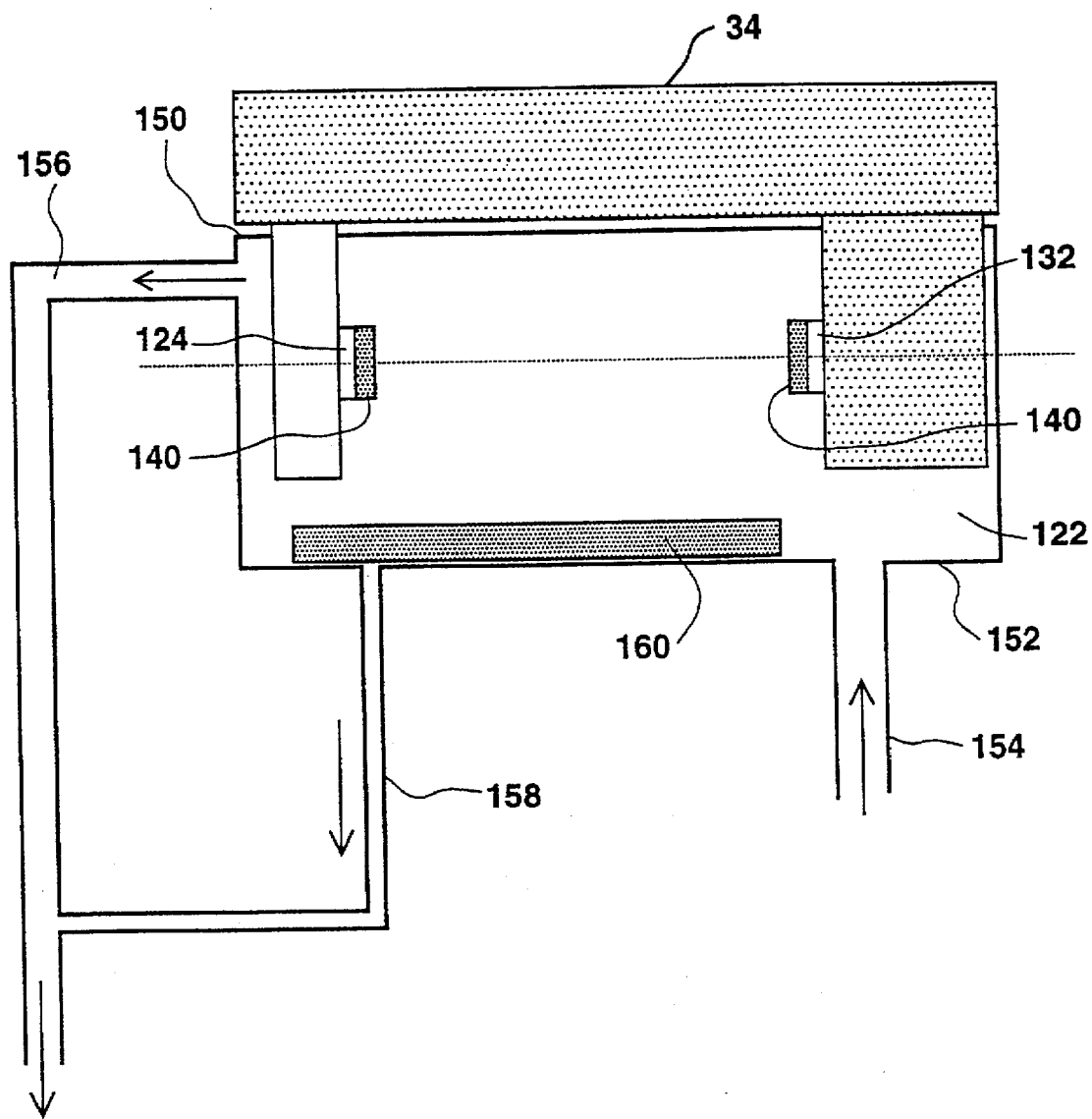
FIG. 8 is a schematic presentation of a sample cell deployed in the optical probe head of the present invention.

Referring now to FIG. 8, in a preferred embodiment, each of windows 132 and 134 of sample cell 122 is covered or made of (i.e., includes) a transparent material 140 having a low surface free energy. One example of such a material is transparent TEFLON (TEFLON AF-1600) manufactured by DuPont having a surface free energy of 15 newtons per $cm^2$, as compared for example with glass, having a surface free energy of 500 newtons per $cm^2$. Thus selecting windows 132 and 134 ensures that hydrophilic particulates and impurities such as water molecules will not adhere to the windows, avoiding muck build-up problems.

Still referring to FIG. 8, in another preferred embodiment, sample cell 122 includes a top and bottom 150 and 152, respectively, a hydrocarbon inlet 154, a top hydrocarbon outlet 156 located at top 150 and a bottom hydrocarbon outlet 158 located at bottom 152. Bottom hydrocarbon outlet 158 is selected narrower than top hydrocarbon outlet 156 and serves as a bottom outlet for removal of pollutants such as water impurities and dirt 160, accumulating at bottom 152, such that the pollutants are at least partially removed from top 150 of cell 122 and such that radiation passing between windows 132 and 134 through the sample is in a pollutants reduced zone, for increasing the accuracy of the measurement.

The sample cell shown in FIG. 8 is typically physically large (e.g., 300 ml volume, 100 mm optical path) and robust. The sample fluid flows into the cell from the bottom, and out through the top. A mild level of turbulence is maintained in the cell, to insure good mixing of the sample. Bubbles which enter the cell rise to the top of the cell, out of the optical path, and exit through the top outlet, along with the fluid. Water and dirt which enter the cell accumulate in the bottom of the cell, out of the optical path, and are washed out of the cell through the bottom outlet in the bottom of the cell. The bottom outlet is much smaller than the top outlet, thus the bulk of the sample flow is from the bottom to the top of the cell, whereas a small flow is maintained through the bottom outlet, in order to remove water and dirt.

A number of advantages result from this arrangement as follows. First, there is no accumulation of water or din in the cell. Second, water, dirt and bubbles are kept mostly out of the optical path. Third, mild turbulence prevents inhomogenieties in the sample, which could otherwise result in the Schlieren effect-optical refraction that could interfere with the measurement. And fourth, the large volume cell has a relatively small surface area, the low surface/volume ratio makes the sample less sensitive to evaporation effects that could occur during calibration or in the presence of a small leak.

As mentioned in the background section, devices which are available for use in the spectral analysis of remote sensing are typically made up of three parts: (i) an analyzer, which include a radiation source and a detection system; (ii) an optical probe head of an appropriate type for transmitting the radiation, to, and receiving it from, a sample; and (iii) suitable optical fibers for guiding the radiation between the analyzer and the probe head.

As further mentioned in the background section, beside the mentioned optical fibers used for guiding the radiation between the probe head and analyzer, at least one additional connection between the analyzer and the probe head is required for controlling the operation of the probe head. Prior art devices employ electrical cables (e.g., in the form of a digital communication link, see John Coats, Timothy Davidson and Lawrence McDermott (1992) The design and application of spectrometrics analyzers of the chemical process industry, Spectroscopy 7(9) Pages 41–49), to achieve the desired control and to provide the optical probe head with electrical power for its operation. However, laying electrical cables in a fuel refinery for example is a complicated task since such cables should be sheltered in special complicated and expensive to build conduits, due to safety requirements. Since at the location of the probe head itself (i.e., on-line), pre-existing power electrical cables are used for various other purposes, which pre-existing cables may additionally be used to provide the probe with the electrical power required for its operation, it is herein disclosed for the first time employing at least one controlling optical fiber, indicated as 170 in FIG. 1, connecting between the analyzer and the optical probe head for controlling the operation of the optical probe head. Any type of optical fiber may be employed for this purpose, nevertheless a telecommunication fiber has performances which are ideal for this purpose. Such a controlling communication fiber may be deployed between any prior art type analyzer and any prior art type optical probe head.

It will be appreciated that such a connection is safer and cheaper than a digital communication link used in prior art systems. As further shown in FIG. 1, the connection between the various parts of the analyzer such as detector 42, light source 22 and computing means (not shown) may still be effected by a common digital communication link 172, since all these components are located in the control region of the refinery.

Thus, in a preferred embodiment, data communication between the analyzer and the probe or field unit takes place through a pair of optical fibers. The only connection between the analyzer and the field unit is an optical cable with for example four fibers: two for spectroscopy and two for communication. This arrangement results in much simpler installation, as only one cable needs to be installed and needs not be sheltered as electrical cables do. Optical fibers have further advantages in that they are immune to electromagnetic interferences, such as those cause by large motors. They also pose no explosion risk, unlike electrical cables.

As mentioned in the background section above, many properties of hydrocarbon mixtures can be determined by analyzing the optical absorption of the mixtures. These properties are related to the spectral data through a calibration process. Spectral data, and the associated properties data, that is, the properties of interest, are used to create a "model" which mathematically relates the two. The model is typically a linear model, generated with a program such as Unscrambler (CAMO A/S, Olav Tryggvasongst 24, N-7011 Trondhein, Norway). Thus prior art optically based analyzers include a linear mathematical model for relating the spectral information to the desired parameters.

Octane number is a performance property of hydrocarbon fuels that expresses the anti-knock qualities of the fuels. It is known that the octane number of a hydrocarbon mixture is a non-linear function of the octane numbers of its' components. See, C. T. Baird IV, Guide to Petroleum Product Blending, page. 17, HPI Consultants, Austin, Tex., 1989. Therefore, linear mathematical models are of limited accuracy in determining octane numbers, as a result of this non-linear behavior.

Thus, according to the present invention determining the octane numbers of a fuel sample is by a method employing an optical system (i.e., any suitable optical system such as but not limited to a laboratory spectrophotometer or any of the embodiments of the system according to the present invention as described hereinabove) for collecting absorption spectral data of the fuel sample and using the spectral data for calculating the octane numbers of the fuel by a non-linear model.

In a preferred embodiment the non-linear model is obtained by training an artificial neural network. For training artificial neural networks see user guide of Neural-UNSC, software for multivariate calibration applying artificial neural network, version 1.02 (1993) CAMO A/S Olav Tryggvasonat 24, N-7011 Trodhein, Norway, which is incorporated by reference as if fully set forth herein.

In a preferred embodiments training of the artificial neural network is effected by (a) providing the artificial neural network with a training set of data, the training set of data are principal components establishing a regression relationship between spectral data and hydrocarbon octane properties of various hydrocarbon samples, the principal components contain the most relevant information, such that the components represent the main systematic variation among the various hydrocarbon samples of the training set of data; (b) providing the artificial neural network with a test set (i.e., validation set) of data, such that the artificial neural network processes the training set of data for optimizing the accuracy in predicting the octane properties of the test set of data. Typically the principal components are obtained using a prior art linear algorithm such as but not limited to a principle component regression (PCR) algorithm or a partial least square (PLS) algorithm.

An important step in developing the non-linear model for octane numbers prediction of hydrocarbon fuels, is determining the architecture of the neural network, that is, the number of neurons included and the way they are connected to each other. Presently determining the architecture of the neural network is done by its operator as well known in the art.

In a preferred embodiment, using the linear algorithm includes collecting reference spectral data which is the absorption spectrum of the optical system, without the sample cell, the linear algorithm is further used by (i) preprocessing each of the samples spectral data by subtracting the reference spectral data for obtaining preprocessed samples spectral data; (ii) determining a baseline for each of the preprocessed samples spectral data by removing high frequency components from the preprocessed samples spectral data, and leaving low frequency components of the preprocessed samples spectral data; (iii) performing baseline corrections by subtracting the baselines from the preprocessed samples spectral data for obtaining base line corrected samples spectral data; (iv) smoothing the base line corrected samples spectral data by removing high frequency noise for obtaining smoothed samples spectral data; (v) integrating the smoothed samples spectral data; (vi) normalizing the smoothed samples spectral data by dividing each point in the smoothed samples spectral data by the integrals for obtaining normalized samples spectral data; and (vii) relating the normalized samples spectral data with fuels octane properties of the various fuel samples and deriving the principal components containing most relevant information.

Figure 9:
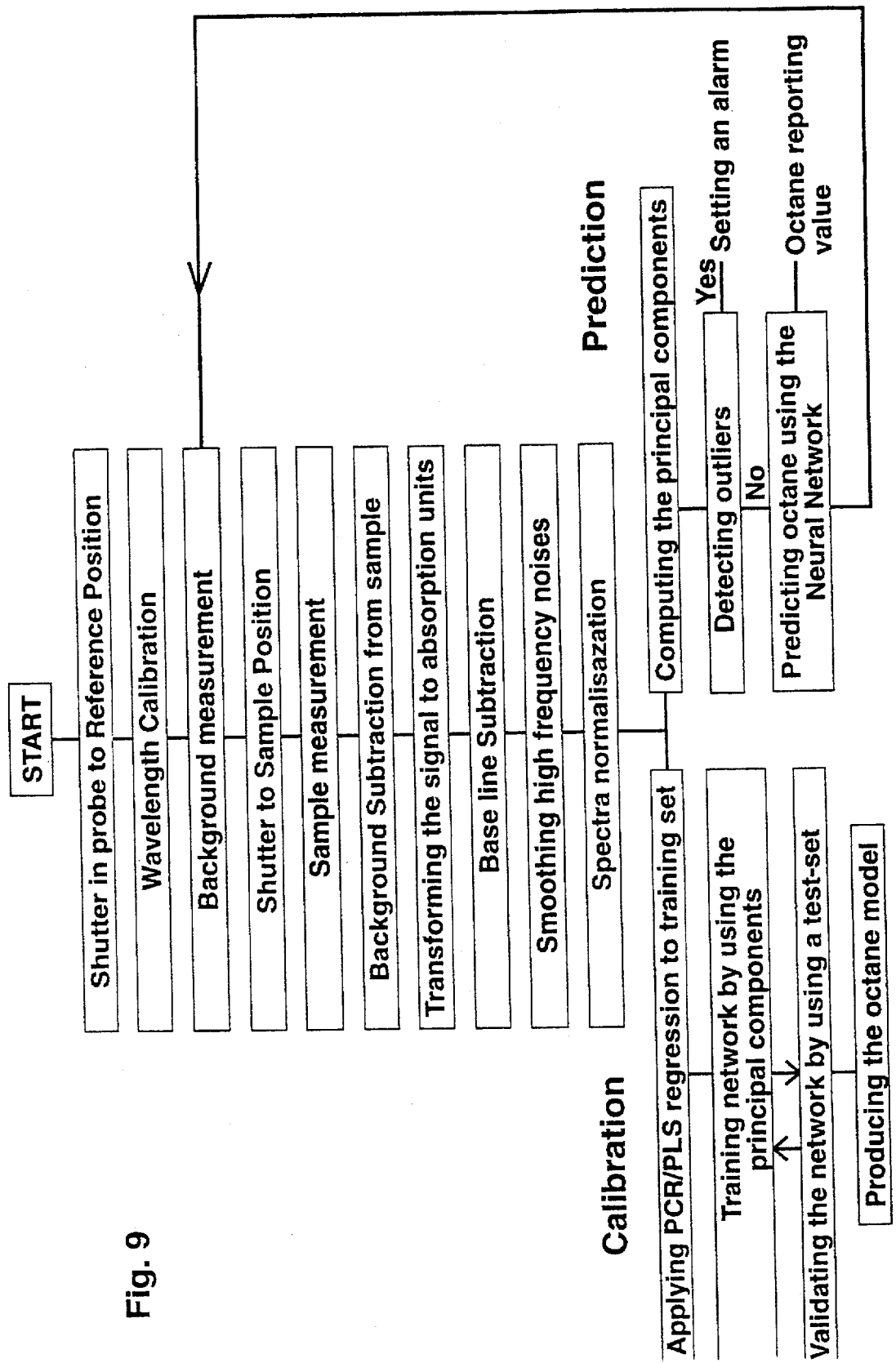
FIG. 9 is a flow chart depicting a preferred embodiment of using the nonlinear model according to the present invention.

With reference now to FIGS. 1, 7 and 9. FIG. 9 presents a flow chart outlining a preferred use of the non-linear model according to the present invention. According to the preferred use, first, partition (i.e., shutter) 126 of probe head 34 is used to block the path of light into cell 122, rendering probe head 34 in its self referencing mode of operation. Second, a wavelength calibration procedure, employing motor 28 operated filter wheel 30, is actuated. Third, the background is measured. Fourth, partition 126 is turned to its sampling mode of operation, i.e., unblocking the path of light into cell 122. Fifth, a hydrocarbon sample accommodated by cell 122 is spectrally measured. Sixth, the background previously determined during self-referencing is subtracted from the sample spectrum. Seventh, the signal thus obtained is transformed into absorption units (AU). Eighth, a base line subtraction procedure is actuated as described above. Ninth, a smoothing high frequency noises procedure is actuated as described above. And tenth, a spectra normalization procedure is actuated as described above.

For producing the non-linear model for octane numbers prediction, attention is called to the lower left part of the flow chart of FIG. 9. In this case, the above description refers to hydrocarbon samples consisting the training and test sets of data. Thus, for producing the non-linear model for octane determination, first, a principal component regression (PCR) or a partial least square (PLS) is performed on the training set of data to obtain principal components as described above. Second, the artificial neural network is trained using these principal components. Third, a test set of data is employed to validate the results in an iterative fashion as indicated by the arrows. And fourth, if the results are validated, the non-linear model is regarded optimized and operative for octane numbers prediction.

For predicting octane numbers of hydrocarbons using the non-linear model, attention is called to the lower right part of the flow chart of FIG. 9. In this case, the above description refers to measuring a sample for octane prediction. Thus, for predicting the octane number of a hydrocarbon sample, first, principal components are determined. Second, if outliers are detected an alarm signal is set on, whereas if outliers are not detected, the octane number prediction process is continued to the third stage, wherein the octane number of the measured sample is predicted using the non-linear model and is reported.

The system of the present invention, unlike earlier NIR instruments, is designed around the use of standard telecommunication optical fibers. Although this limits somewhat the spectral range that the system can measure, all the essential information regarding materials of interest in the petrochemical industry can be found in this spectral range.

The use of standard telecommunication optical fibers results in many practical advantages. The main analyzer unit can be located up to 2 miles from the field unit (i.e., probe). As a result, the main unit can be located in a general purpose area, such as a control room, and does not require any special housings, utilities, or maintenance. The optical fibers are readily available, inexpensive, and easily installed. These fibers are also humidity free, and thus immune to temperature effects that some silica fibers exhibit in the NIR range.

A typical installation of the system according to the present invention in a refinery includes installing the main analyzer unit in for example a control room in a general purpose area of the refinery, which analyzer is spectrally communicating through optical fibers as described above with field traits (i.e., optical probe head) located at various locations along lines in the refinery.

In a preferred embodiment, a field unit is also located in a laboratory in the general purpose area (i.e., off-line), which unit is spectrally communicating with the main analyzer unit and replacing other spectral instruments typically used thereat for manual hydrocarbons analysis. This arrangement becomes feasible due to the use of telecommunication optical fibers which can efficiently transmit light in the NIR range for up to two miles (3 kilometers). This arrangement has advantages since the unit located in the laboratory can be used for validation, calibration, measurements of tank stored fuels, etc., as other instruments, while at the same reducing repeatability problems associated with employing different instruments, since a single main analyzer unit is employed.

The use of a single strand optical fiber in spectroscopy is not trivial. The fiber itself may be a major source of modal noises that must be dealt with. A reference device is required in order to subtract the modal noises. To simplify the system design, it is preferable that such a reference device will be able to compensate for the other optical elements of the system (light source, spectrograph, detector, etc.)

A modern optical system effectively compensates for these effects. The innovative probe design as disclosed in U.S. Pat. No. 5,381,237, to Sela allows efficient optical coupling to the sample cell, and background correction for fiber optic effects. The sample cell design is a self-referencing device designed for transmission measurements. Innovative sample cell design and construction materials have created a sample—conditioning free system. This sample cell, and associated algorithms, enable temperature compensation without additional temperature probes. Moderate levels of water (up to 5%), bubbles and particulates in the sample flow do not interfere with the measurements. Therefore, using NIR spectroscopy according to the system of the present invention omits the requirement for using a sample conditioning system (SCS) (for use of SCS see, for example, John Coats, Timothy Davidson and Lawrence McDermott (1992) The design and application of spectrometrics analyzers of the chemical process industry, Spectroscopy 7(9) Pages 41–49) to remove impurities such as air bobbles, particulates, inhomogeneities and water from an examined sample and yields more accurate results.

A sample that differs significantly from the "training set" (the set of samples used to originally calibrate the instrument), will also be measured by the instrument, even though it falls out of the instruments calibration range. These samples are called "outliers". In the event of outlier detection, the field unit may automatically grab a sample for laboratory analysis, enabling a later model update, which will then include the "outlier" in the models calibration range.

A further feature of the design is that all communication between the field unit(s) and the main analyzer unit is through additional fibers in the fiber optic cable. There is no need for any electrical connection between the units. The field unit is powered by electric power readily available on-site.

The system requires essentially no maintenance. It does not require any of the complicated mechanical assemblies typically found in process analyzers, including NIR systems.

The only murine maintenance required is periodically replacing the light source.

While the invention has been described with respect to a limited number of embodiments, it will be appreciated that many variations, modifications and other applications of the invention may be made.

Reference is now made to the following examples, which together with the above descriptions, illustrate the invention.

EXAMPLE 1

Figure 10:
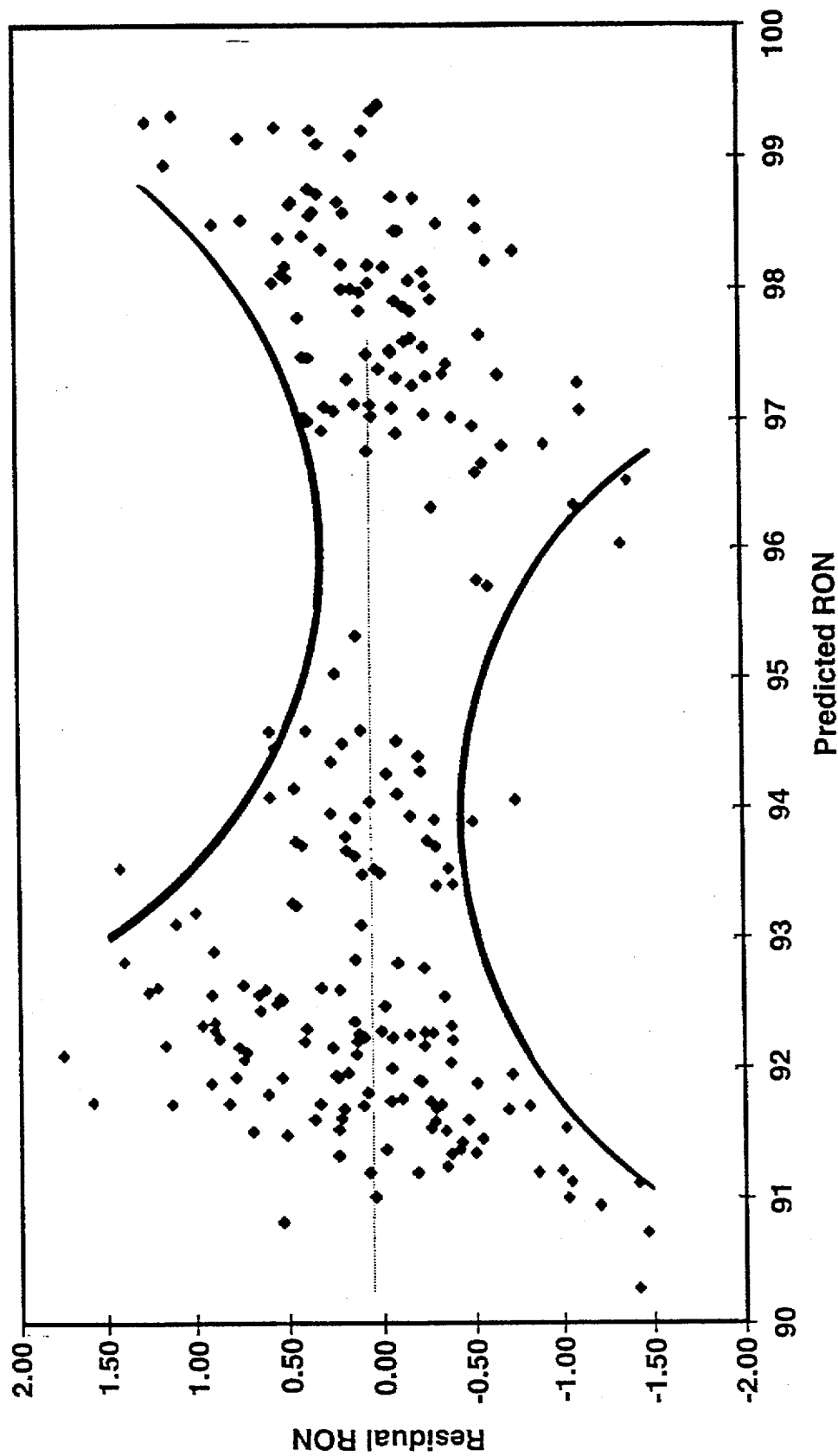
FIG. 10 is a graphic depiction of correlations between residual research octane numbers and predicted research octane numbers for various fuels, prediction is by a prior art PLS 1 linear model.
Figure 11:
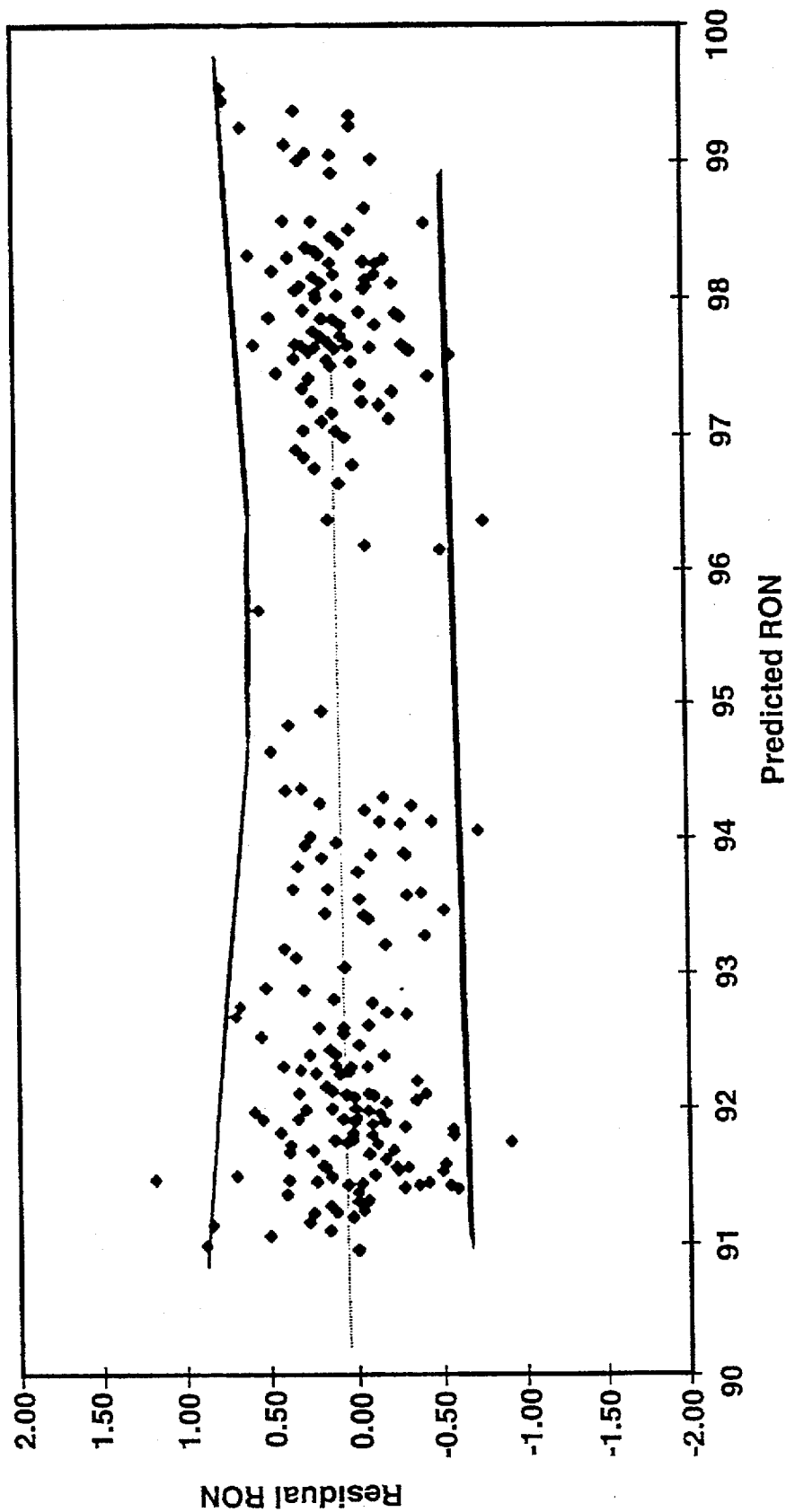
FIG. 11 is a graphic presentation of correlations between residual research octane numbers and predicted research octane numbers for various fuels, prediction is by a non-linear model prepared by the non-linear neural network technique according to the present invention.

With reference to FIGS. 10 and 11 presented are correlations between residual research octane numbers (RON), (i.e., the difference between the RON as determined spectroscopically and the RON as determined by a research knock engine (Core Laboratories) according to ASTM D02699), and predicted RON as determined spectroscopically, for various fuels, wherein in FIG. 10, RON prediction was by a linear model—PLS1 in this case, and in FIG. 11 RON prediction was by a non-linear model prepared by the non-linear neural network technique as described above. Similar results were obtained for motor octane number (MON), according to ASTM 02700, not shown.

Note the differences in distribution of points in the graphs of FIGS. 10 and 11, as bordered by the bold lines. The root mean square error of prediction (RMSEP) in the case of the linear model shown in FIG. 10 is 0.19, whereas the RMSEP using the non-linear model as shown in FIG. 11 is only 0.15, a considerable improvement over the linear model.

EXAMPLE 2

The accuracy of the system of the present invention in determining various physical, chemical and performance properties of various fuels was evaluated by statistical methods and the results are presented in Table 2, below.

TABLE 2

System accuracy

| Property | Units | Range | RMSEP | Corr. Coef. |
|---|---|---|---|---|
| RON | Octane Number | 90–100 | 0.27 | 0.996 |
| MON | Octane Number | 80–90 | 0.23 | 0.998 |
| RVP | psi | 5–11 | 0.15 | 0.99 |
| total aromatics | vol % | 5–45 | 1.48 | 0.98 |
| total olefins | vol % | 0–30 | 0.94 | 0.99 |
| benzene | vol % | 0–1.2 | 0.06 | 0.95 |
| Dist. Temp. 10% | °F. | 100–180 | 3.32 | 0.97 |
| Dist. Temp. 50% | °F. | 150–260 | 4.5 | 0.98 |
| m-xylene | vol % | 0–100 | 0.98 | 0.999 |
| o-xylene | vol % | 0–100 | 0.33 | 0.999 |
| p-xylene | vol % | 0–100 | 1.06 | 0.998 |
| ehthyl benzene | vol % | 0–100 | 0.32 | 0.999 |
| PDEB | vol % | 0–100 | 0.86 | 0.999 |

Table 2 statistically presents these results by attributing each of the examined properties, each was measured in at least 100 points within the ranges indicated in table 2, an RMSEP value and a correlation coefficient value as determined comparing results obtained by the system of the present invention with results obtained by standard methods (e.g., ASTM D02699 and ASTM 02700 for RON and MON, respectively). Note the high correlation coefficient values obtained for all properties examined, indicating the validity of the system according to the present invention in determining fuel properties.

EXAMPLE 3

Figure 12:
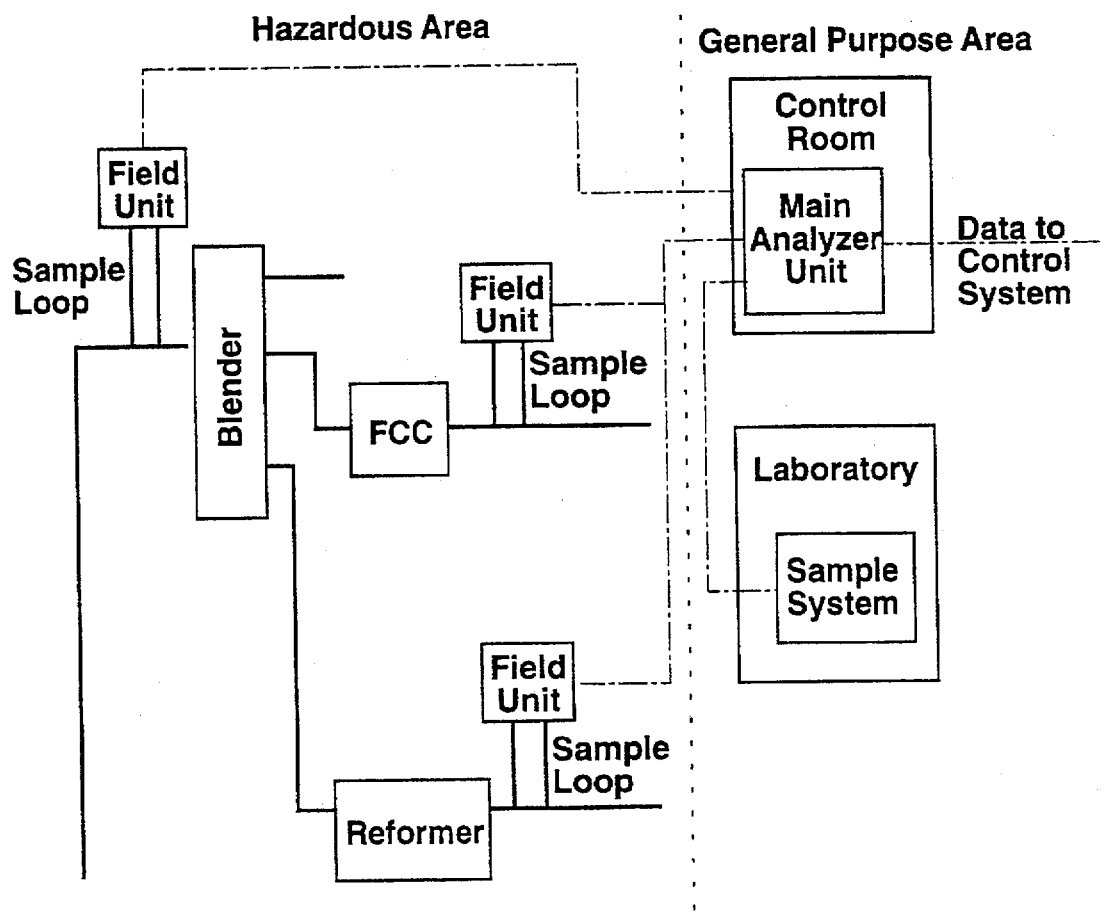
FIG. 12 is a schematic presentation of a typical installation of the system according to the present invention in a refinery.
Figure 13:
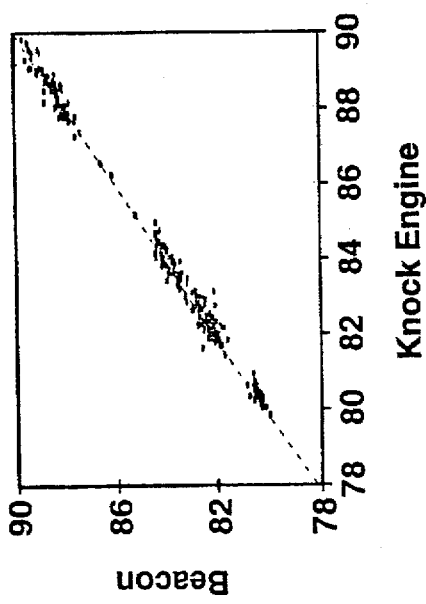
FIG. 13 presents plots of the motor octane number (MON) of fuels derived at different stages from three refinery lines: a fluid catalytic cracking (FCC) line, a reformer line and a blender line, as was determined using the system and the non-linear model of the present invention, as a function of the MON of the same fuels as was determined by the prior art ASTM 02700 method using a conventional motor knock engine.

With reference now to FIGS. 12 and 13. FIG. 12 schematically presents a typical installation of the system according to the present invention in a refinery. The main analyzer unit is installed in for example a control room in a general purpose area of the refinery and is spectrally communicating through optical fibers as described above with three field units (i.e., optical probe heads) located at a reformer line, a fluid catalytic cracking (FCC) line and in a blender line, all three lines located in the hazardous area of the refinery. The main analyzer unit provides data regarding these lines to the refinery control system which controls the lines and to a laboratory, whereat manual examination of samples may be performed in parallel, using for example an additional field unit as described above, which additional unit is spectrally connected to the same analyzer.

FIG. 13 presents the motor octane numbers (MON) of fuels derived at different stages from the three different refinery lines: fluid catalytic cracking (FCC)—dark dots, reformer—lighter dots, and blender—light dots, as was determined using the system of the present invention and the non-linear model described above as a function of the MON of the same fuels as was determined by the ASTM 02700 method using a motor knock engine.

Note that all the dots fall within a narrow range from the diagonal, indicating the validity and universality of the measurements performed with the system of the present invention.

EXAMPLE 4

Figure 14:
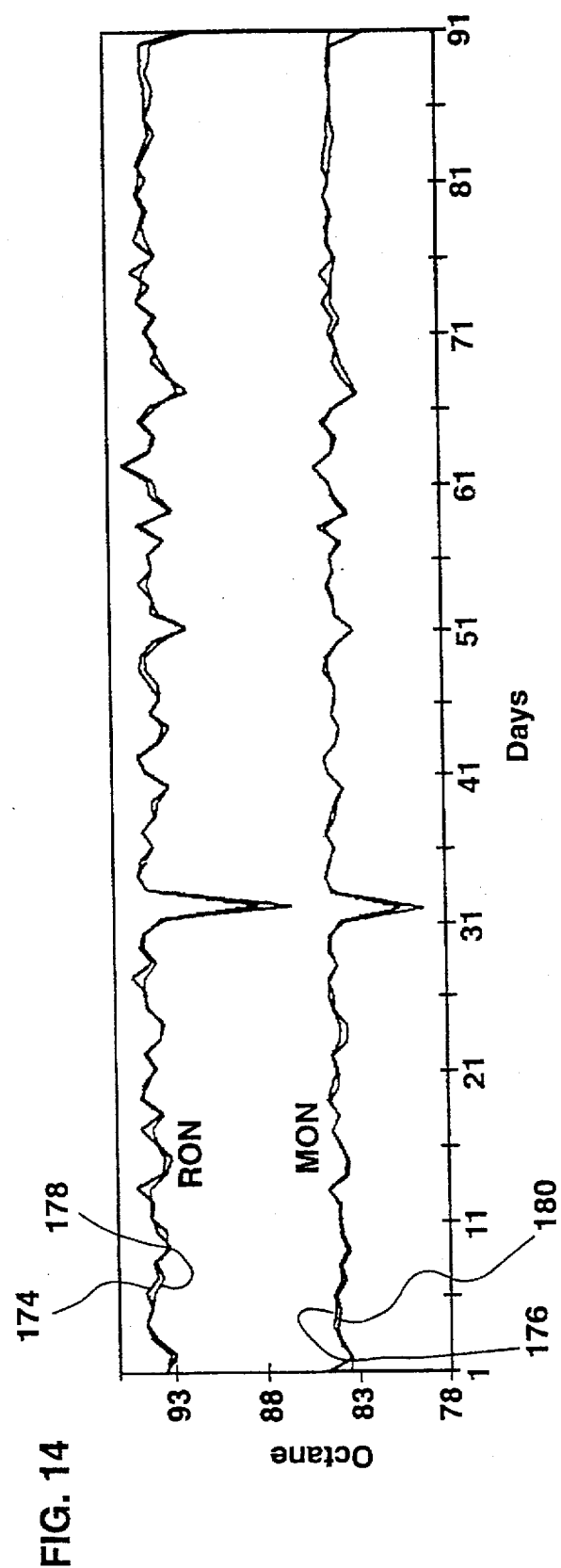
FIG. 14 presents plots of research (RON) and motor (MON) octane numbers over a three month period in a fuel refinery, as measured using the system and the non-linear model of the present invention, and plots of conventional ASTM D02699 and ASTM 02700 methods over the same time period.

With reference now to FIG. 14, presented are plots of research (RON) and motor (MON) octane numbers over a three month period in a refinery as measured using the system and the non-linear model of the present invention (plots 174 and 176, respectively), and conventional methods, i.e., ASTM D02699 and ASTM 02700 (plots 178 and 180), respectively.

Note that a strong correlation exists for both RON and MON measurements using the system of the present invention and the conventional methods including in day 32 where a drop in both RON and MON was recorded.

What is claimed is:

1. A system for remote, real-time near infra red spectral analysis of hydrocarbons, comprising:
   (a) a light source for generating near infra red radiation;
   (b) an optical probe head being at on-line contact with an analyzed hydrocarbon sample;
   (c) at least one standard telecommunication transmitting optical fiber for inputting said near infra red radiation into said optical probe head, such that said radiation passes at least once through said hydrocarbon sample, such that a spectrum of said sample is generated;
   (d) a detector for analyzing said spectrum, said detector and said light source being part of an analyzer; and
   (e) at least one standard telecommunication receiving optical fiber for receiving said radiation after said passing through said sample and inputting said radiation into said detector;

each of said standard telecommunication optical fibers being made of graded index doped silica and having a core diameter of about 50 to 100 micrometers.

2. A system as in claim 1, wherein said light source includes:
   (a) an illuminator for said generation of said radiation, said radiation is propagating in a parallel fashion;
   (b) a motor operated filter wheel for wavelength calibration;
   (d) a collimating optical system for directing said radiation into said transmitting optical fiber.

3. A system as in claim 2, wherein said illuminator includes a convex lens for effecting said parallel propagation of said radiation.

4. A system as in claim 2, wherein said collimating optical system includes a first gradient index lens.

5. A system as in claim 4, wherein said at least one transmitting optical fiber is held in a first ferule which is connected to said first gradient index lens.

6. A system as in claim 4, wherein said telecommunication optical fibers have a gradient index.

7. A system as in claim 1, further comprising one additional optical probe head being off-line in a general purpose area of a fuel plant and being in spectral communication with said analyzer via additional telecommunication optical fibers, said one additional optical probe head being for manual analysis of the hydrocarbons.

8. A system as in claim 1, wherein said optical probe head includes:
   (a) a gradient index lens, at least one face of which is in optical contact with said hydrocarbon sample;
   (b) a mirror placed so as to reflect radiation coming through said gradient index lens back to said gradient index lens through said hydrocarbon sample;
wherein, said at least one transmitting optical fiber is for inputting radiation into said gradient index lens of said optical probe head, and said at least one transmitting optical fiber and said at least one receiving optical fiber are fixedly held relative to said gradient index lens, so that said gradient index lens and said optical fibers are aligned, such that radiation input into said gradient index lens by said transmitting optical fiber which passes through said gradient index lens and said hydrocarbon sample to said mirror is reflected by said mirror through said hydrocarbon sample and through said gradient index lens, and is received by said at least one receiving optical fiber.

9. A system as in claim 8, wherein said at least one transmitting optical fiber and said at least one receiving optical fiber are held in a ferule which is connected to said gradient index lens.

10. A system as in claim 8, wherein said aligning of said optical fibers and said gradient index lens is effected by introducing radiation through one of said optical fibers, moving said optical fibers and said gradient index lens relative to each other until maximum radiation intensity is detected in the other of said optical fibers and fixing the position of said optical fibers and said gradient index lens.

11. A system as in claim 8, wherein said optical probe head includes a sample cell for accommodating said analyzed hydrocarbon sample, said cell includes a first and a second transparent windows, said at least one face of said gradient index lens is in indirect contact with said hydrocarbon sample through said first window and said mirror is behind said second window.

12. A system as in claim 11, wherein each of said first and second windows includes a material having a low surface free energy.

13. A system as in claim 12, wherein said material having a low surface free energy is a transparent fluorocarbon polymer.

14. A system as in claim 11, wherein said sample cell includes a top and a bottom, a hydrocarbon inlet, a top hydrocarbon outlet located at said top and a bottom hydrocarbon outlet located at said bottom, said bottom hydrocarbon outlet is narrower than said top hydrocarbon outlet and serves for removal of pollutants accumulating at said bottom, such that pollutants are at least partially removed from said top of said cell and such that said passing of said radiation through said hydrocarbon sample is in a pollutants reduced zone.

15. A system as in claim 1, wherein said optical probe head includes:
   (a) a gradient index lens;
   (b) a mirror placed so as to reflect radiation coming through said gradient index lens back to said gradient index lens through said hydrocarbon sample;
   (c) a moveable partition located between said gradient index lens and said mirror, said partition serving to alternately block and unblock radiation between said mirror and said gradient index lens;
wherein, said at least one transmitting optical fiber is for inputting radiation into said gradient index lens, and said at least one transmitting optical fiber and said at least one receiving optical fiber are fixedly held relative to said gradient index lens so that said gradient index lens and said optical fibers are aligned such that radiation input into said gradient index lens by said transmitting optical fiber which passes through said gradient index lens and said hydrocarbon sample to said mirror is reflected by said mirror through said hydrocarbon sample and through said gradient index lens and is received by said at least one receiving optical fiber when said moveable partition is not blocking radiation between said mirror and said gradient index lens and such that radiation input into said gradient index lens by said transmitting optical fiber which is reflected from the interface of said gradient index lens and the sample is received by said at least one receiving optical fiber.

16. A system as in claim 15, wherein said at least one transmitting optical fiber and said at least one receiving optical fiber are held in a ferule which is connected to said gradient index lens.

17. A system as in claim 15, wherein said aligning of said optical fibers and said gradient index lens is effected by introducing radiation through one of said optical fibers, moving said optical fibers and said gradient index lens relative to each other until maximum radiation intensity is detected in the other of said optical fibers and fixing the position of said optical fibers and said gradient index lens.

18. A system as in claim 15, wherein said optical probe head includes a sample cell for accommodating said analyzed hydrocarbon sample, said cell includes a first and a second transparent windows, at least one face of said gradient index lens is in indirect contact with said hydrocarbon sample through said first window and said mirror is behind said second window.

19. A system as in claim 18, wherein each of said first and second windows includes a material having a low surface free energy.

20. A system as in claim 19, wherein said material having a low surface free energy is a transparent fluorocarbon polymer.

21. A system as in claim 18, wherein said sample cell includes a top and a bottom, a hydrocarbon inlet, a top hydrocarbon outlet located at said top and a bottom hydrocarbon outlet located at said bottom, said bottom hydrocarbon outlet is narrower than said top hydrocarbon outlet and serves for removal of pollutants accumulating at said bottom, such that pollutants are at least partially removed from said top of said cell and such that said passing of said radiation through said hydrocarbon sample is through a pollutants reduced zone.

22. A system as in claim 1, wherein said optical probe head includes a sample cell for accommodating said analyzed hydrocarbon sample, said cell includes a first and a second transparent windows, a mirror and a gradient index lens, at least one face of said gradient index lens is in indirect contact with said hydrocarbon sample through said first window and said mirror is behind said second window.

23. A system as in claim 22, wherein each of said first and second windows includes a material having a low surface free energy.

24. A system as in claim 23, wherein said material having a low surface free energy is a transparent fluorocarbon polymer.

25. A system as in claim 22, wherein said sample cell includes a top and a bottom, a hydrocarbon inlet, a top hydrocarbon outlet located at said top and a bottom hydrocarbon outlet located at said bottom, said bottom hydrocarbon outlet is narrower than said top hydrocarbon outlet and serves for removal of pollutants accumulating at said bottom, such that pollutants are at least partially removed from said top of said cell and such that said passing of said radiation through said hydrocarbon sample is through a pollutants reduced zone.

26. A system as in claim 1, wherein said system is for determining at least one property of said sample, said at least one property is selected from the group consisting of hydrocarbon physical properties, hydrocarbon chemical properties and hydrocarbon performance properties.

27. A system as in claim 26, wherein:
   (a) said performance properties are selected from the group consisting of motor octane number and research octane number;
   (b) said physical properties are selected from the group consisting of Reid vapor pressure, viscosity, API gravity, freeze point, pour point, flash point, cloud point and distillation point; and
   (c) said chemical properties are selected from the group consisting of fraction of total aromatics volume, fraction of benzene volume, fraction of MTBE volume, fraction of olefins volume and PIONA.

28. A system for remote real-time spectral analysis of a hydrocarbon comprising:
   (a) a light source for generating light radiation;
   (b) an optical probe head being at on-line contact with an analyzed hydrocarbon sample, wherein said optical probe head includes a sample cell for accommodating said analyzed hydrocarbon sample, said cell includes a top and a bottom, a hydrocarbon inlet, a top hydrocarbon outlet located at said top and a bottom hydrocarbon outlet located at said bottom, said bottom hydrocarbon outlet is narrower than said top hydrocarbon outlet and serves for removal of pollutants accumulating at said bottom, such that pollutants are at least partially removed from said top of said cell and such that said passing of said radiation through said hydrocarbon sample is through a pollutants reduced zone;
   (c) at least one transmitting optical fiber for inputting said light radiation into said optical probe head, such that said radiation passes at least once through said hydrocarbon sample and a spectrum of said hydrocarbon sample is generated;
   (d) a detector for analyzing said spectrum, said detector and said light source being part of an analyzer; and
   (e) at least one receiving optical fiber for receiving said radiation after said passing of said radiation through said sample and inputting said radiation into said detector.

29. A system for remote real-time spectral analysis of hydrocarbons comprising:
   (a) a light source for generating light radiation;
   (b) an optical probe head being at on-line contact with an analyzed hydrocarbon sample;
   (c) at least one transmitting optical fiber for inputting said light radiation into said optical probe head, such that said radiation passes at least once through said hydrocarbon sample, such that at least some of said radiation is absorbed by said hydrocarbon sample and a spectrum associated with said sample is generated;
   (d) a detector for analyzing said spectrum, said detector and said light source being part of an analyzer;
   (e) at least one receiving optical fiber for receiving said radiation after said passing through said sample and inputting said radiation into said detector; and
   (f) at least one controlling optical fiber connecting between said analyzer and said optical probe head for controlling said optical probe head.

* * * * *